US005739106A

United States Patent [19]
Rink et al.

[11] Patent Number: 5,739,106
[45] Date of Patent: Apr. 14, 1998

[54] APPETITE REGULATING COMPOSITIONS

[76] Inventors: Timothy J. Rink, 6041 Camino De La Costa, La Jolla, Calif. 92037; Andrew A. Young, 510 Josh Way, Alpine, Calif. 91901; Nigel Robert Arnold Beeley, 227 Loma Corta Dr., Solana Beach, Calif. 92037; Kathryn S. Prickett, 7612 Trailbrush Ter., San Diego, Calif. 92126

[21] Appl. No.: 477,727

[22] Filed: Jun. 7, 1995

[51] Int. Cl.$^6$ .................. A61K 38/00; A61K 38/28; C07K 5/00; C07K 7/00
[52] U.S. Cl. .................. 514/12; 514/16; 514/18; 514/19; 530/303; 530/307; 530/312; 530/324; 530/331; 530/328
[58] Field of Search .................. 530/303, 307, 530/312, 331, 324, 328; 514/12, 16, 18, 19

[56] References Cited

U.S. PATENT DOCUMENTS

| | | | |
|---|---|---|---|
| 5,264,372 | 11/1993 | Beaumont et al. | 436/504 |
| 5,321,008 | 6/1994 | Beaumont et al. | 514/4 |
| 5,367,052 | 11/1994 | Cooper et al. | 530/307 |
| 5,376,638 | 12/1994 | Young et al. | 514/12 |
| 5,580,953 | 12/1996 | Albrecht et al. | 530/303 |

FOREIGN PATENT DOCUMENTS

WO 93/10146 5/1993 WIPO.
WO 94/26292 11/1994 WIPO.

OTHER PUBLICATIONS

U.S. application Ser. No. 08/447,080, filed May 30, 1995.
Arano, et al., *Bioconj. Chem.* 2:71–76 (1991).
Balasubramaniam, et al., *Peptides* 12:919–924 (1991).
Barrett–Connor, *Am. J. Epidemiol.* 113:276–284 (1981).
Beaumont, et al., *Mol. Pharmacol.* 44:493–497 (1993).
Brain, et al., *Eur. J. Pharmacol.* 183:2221 (1990).
Bray, *Dis. Mon.* 26:1–85 (1979).
Butler, et al., *Am. J. Epidemiol.* 16:971–980 (1982).
Chance, et al., *Brain Res.* 539:352–354 (1991).
Chantry, et al., *Biochem. J.* 277:139–143 (1991).
Chiang, et al., *Circulation* 39:403–421 (1969).
Cooper, et al., *Proc. Nat Acad. Sci.* 85:7763–7766 (1988).
Cooper, et al., *Proc. Natl Acad. Sci., USA* 84:8628–8632 (1987).
Cooper, et al., *Biochem. Biophys. Acta* 1014:247–258 (1989).
Cox, *Behav. Brain Res.* 38:35–44 (1990).
Crawley and Corwin, *Peptides* 15: 731–755 (1994).
Deems, et al., *Biochem. Biophys. Res. Commun.* 181:116–120 (1991).
Dulawa, et al., *Peptides* 15:913–918 (1994).
Follett, et al., *Clinical Research* 39:39A (1991).
Frontoni, et al., *Diabetes* 40:568–573 (1991).
Galeazza, et al., *Peptides* 12:585–591 (1991).

Gardiner, et al., *Diabetes* 40:948–951 (1991).
Gedulin, et al., *Biochem. Biophys. Res. Commun.* 180:782–789 (1991).
Gill, et al., *Life Sciences* 48:703–710 (1991).
Gomez–Foix, et al., *Biochem. J.* 276:607–610 (1991).
Hartter, et al., *Diabetologia* 34:52–54 (1991).
Hinton, et al., *Brain Res. Bull.* 17:615–619 (1986).
Huang, et al., *Hypertension* 19:I101–I109 (1991).
Jarrett, et al., *Int. J. Epidemiol.* 7:15–24 (1978).
Kanatsuka, et al., *FEBS Letts.* 259:199–201 (1989).
King, et al., *Cancer Research* 54:6176–6185 (1994).
Koda, et al., *The Lancet* 339:1179–1180 (1992).
Kolata, *Science* 227:1019–1020 (1985).
Koopmans, et al., *Diabetologia* 34:218–224 (1991).
Leighton, et al., *Nature* 335:632–635 (1988).
LeSauter and Geary, *Am. J. Physiol.* 253:R719–725 (1987).
Lieverse, et al., *Ann. N.Y. Acad. Sci.* 713:268–272 (1994).
Lupien and Young, *Diabetes Nutrition and Metabolism—Clinical and Experimental* 6:13–18 (1993).
Lutz, et al., *Physiology & Behavior* 55:891–895 (1994).
Medalie, et al., *Arch. Int. Med.* 135:811–817 (1975).
Modan, et al., *J. Clin. Invest.* 75:809–817 (1985).
Molina, et al., *Diabetes* 39:260–265 (1990).
Moore, et al., *Biochem. Biophys. Res. Commun.* 179:1–9 (1991).
Morley, et al., *Pharmacol. Biochem. Behav.* 44:577–580 (1993).
Morley and Flood, *Peptides* 12:865–869 (1991).
Morley, et al., *Am. J. Physiol.* 267:R178–R184 (1994).
Moyses and Kolterman, *Drugs of the Future* (May 1995).
Ogawa, et al., *J. Clin. Invest.* 85:973–976 (1990).
Pittner, et al., *J. Cell. Biochem.* 55S:19–28 (1994).
Reidelberger, *J. Nutr.* 124(8) 1327S–1333S (1994).
Roden, et al., *Diabetologia* 35:116–120 (1992).
Sanke, et al., *Diabetologia* 34:129–132 (1991).
Sims, *Hypertension* 4(3):111–43–111–49 (1982).
Smith and Gibbs, *Annals N.Y. Acad. Sci.* 713:236–241 (1994).
Stephens, et al., *Diabetes* 40:395–400 (1991).
Wang, et al., *FEBS Letts.* 219:195–198 (1991).
Weber, et al., *Bioconj. Chem.* 1:431–437 (1990).
Young, et al., *Am. J. Physiol.* 259:E457–E461 (1990).
Young, et al., *FEBS Letts.* 281:149–151 (1991).
Young, et al., *J. Cell. Biochem.* 55S:12–18 (1994).
Young, et al., *Am. J. Physiol.* 263:E274–E281 (1992).
Young, et al., *Diabetologia* 38:642–648 (1995).
Zhu, et al., *Biochem. Biophys. Res. Commun.* 177:771–776 (1991).

(List continued on next page.)

*Primary Examiner*—Cecilia J. Tsang
*Assistant Examiner*—Jennifer Harle
*Attorney, Agent, or Firm*—Lyon & Lyon LLP

[57] ABSTRACT

Compositions and methods for reducing food intake, suppressing appetite and controlling body weight are provided. Such compositions may include an amylin agonist and a CCK agonist or a hybrid peptide.

85 Claims, 1 Drawing Sheet

OTHER PUBLICATIONS

Zierath, et al., *Diabetologia* 35:26–31 (1992).

Zimmett, *Diabetologia* 22:399–411 (1982).

Azria, *Calcitonins—Physiological and Pharmacological Aspects*, pp. 1–34, Springer–Verlag (1989).

*Harrison's Principles of Internal Medicine*, 12th Ed., McGraw Hill, Inc. (1991) p. 411.

Quadri, et al., "Optimization of biodistribution by introducing different chemical linkages betwen antibody and an indium–111 chelate," *Cancer Imaging with Radiolabeled Antibodies*, Goldenberg (ed.), (1990), pp. 201–213.

Walsh, "Gastrointestinal Hormones," *Physiology of the Gastrointestinal Tract* 3d Ed., Raven Press, (1994) New York.

West, *Epidemiology of Diabetes and its Vascular Lesions*, Elsevier/North Holland, New York, pp. 191–284, 351–389 (1978).

SEQUENCE LISTING ( 1 ) GENERAL INFORMATION:

( i i i ) NUMBER OF SEQUENCES: 108

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

```
Lys Ala Pro Ser Gly Arg Met Ser Ile Val Lys Asn Leu Gln Asn Leu
 1               5                  10                      15
Asp Pro Ser His Arg Ile Ser Asp Arg Asp Tyr Xaa Met Gly Trp Met
                20                  25                  30
Asp Phe
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

```
Asp Tyr Xaa Met Gly Trp Met Asp Phe
 1               5
```

( 2 ) INFORMATION FOR SEQ ID NO:3:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:3:

```
Lys Cys Asn Thr Ala Leu Ala Thr Cys Ala Thr Gln Arg Leu Ala Asn
 1               5                  10                      15
Phe Leu Val His Ser Ser Asn Asn Phe Gly Ala Ile Leu Ser Ser Thr
                20                  25                  30
Asn Val Gly Ser Asn Thr Tyr
                35
```

( 2 ) INFORMATION FOR SEQ ID NO:4:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:4:

```
Lys Cys Asn Thr Ala Thr Cys Ala Thr Gln Arg Leu Ala Asn Phe Leu
 1               5                  10                  15
Val His Ser Ser Asn Asn Phe Gly Pro Ile Leu Pro Pro Thr Asn Val
                20                  25                  30
Gly Ser Asn Thr Tyr
                35
```

(2) INFORMATION FOR SEQ ID NO:5:

(i) SEQUENCE CHARACTERISTICS:
        (A) LENGTH: 37 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:5:

```
Lys Cys Asn Thr Ala Thr Cys Ala Thr Gln Lys Leu Ala Asn Phe Leu
 1               5                  10                  15
Val His Ser Ser Asn Asn Phe Gly Pro Ile Leu Pro Pro Thr Asn Val
                20                  25                  30
Gly Ser Asn Thr Tyr
                35
```

(2) INFORMATION FOR SEQ ID NO:6:

(i) SEQUENCE CHARACTERISTICS:
        (A) LENGTH: 32 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:6:

```
Cys Ser Asn Leu Ser Thr Cys Val Leu Gly Lys Leu Ser Gln Glu Leu
 1               5                  10                  15
His Lys Leu Gln Thr Tyr Pro Arg Thr Asn Thr Gly Ser Gly Thr Pro
                20                  25                  30
```

(2) INFORMATION FOR SEQ ID NO:7:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:7:

Asp Xaa Met Gly Trp Met Asp Phe
 1           5

( 2 ) INFORMATION FOR SEQ ID NO:8:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:8:

Asp Tyr Met Gly Trp Met Asp Phe
 1           5

( 2 ) INFORMATION FOR SEQ ID NO:9:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:9:

Met Gly Trp Met Asp Phe
 1           5

( 2 ) INFORMATION FOR SEQ ID NO:10:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:10:

```
Gly Trp Met Asp Phe
 1               5
```

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:11:

```
Trp Met Asp Phe
 1
```

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:12:

```
Lys Asp Xaa Met Gly Trp Met Asp Phe
 1               5
```

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:13:

Lys Asp Tyr Met Gly Trp Met Asp Phe
 1               5

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:14:

Lys Met Gly Trp Met Asp Phe
 1           5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:15:

Lys Gly Trp Met Asp Phe
 1       5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:16:

Lys Trp Met Asp Phe
 1           5

( 2 ) INFORMATION FOR SEQ ID NO:17:

( i ) SEQUENCE CHARACTERISTICS:
   ( A ) LENGTH: 37 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:17:

```
Lys Cys Asn Thr Ala Thr Cys Ala Thr Gln Arg Leu Ala Asn Glu Leu
 1               5                  10                  15
Val His Ser Ser Asn Asn Phe Gly Pro Ile Leu Pro Pro Thr Asn Val
             20                  25                  30
Gly Ser Asn Thr Tyr
             35
```

( 2 ) INFORMATION FOR SEQ ID NO:18:

( i ) SEQUENCE CHARACTERISTICS:
   ( A ) LENGTH: 32 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:18:

```
Cys Ser Asn Leu Ser Thr Cys Val Leu Gly Lys Leu Ser Gln Glu Leu
 1               5                  10                  15
His Lys Leu Gln Thr Tyr Pro Arg Thr Asn Thr Gly Ser Gly Thr Pro
             20                  25                  30
```

( 2 ) INFORMATION FOR SEQ ID NO:19:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:19:

```
Asp Xaa Met Gly Trp Met Asp Phe
 1               5
```

( 2 ) INFORMATION FOR SEQ ID NO:20:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:20:

Asp Tyr Met Gly Trp Met Asp Phe
1                  5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:21:

Met Gly Trp Met Asp Phe
1              5

( 2 ) INFORMATION FOR SEQ ID NO:22:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:22:

Gly Trp Met Asp Phe
1           5

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:23:

Trp Met Asp Phe
1

( 2 ) INFORMATION FOR SEQ ID NO:24:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:24:

Lys Asp Xaa Met Gly Trp Met Asp Phe
1               5

( 2 ) INFORMATION FOR SEQ ID NO:25:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:25:

Lys Asp Tyr Met Gly Trp Met Asp Phe
1               5

( 2 ) INFORMATION FOR SEQ ID NO:26:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:26:

Lys Met Gly Trp Met Asp Phe
1               5

( 2 ) INFORMATION FOR SEQ ID NO:27:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:27:

Lys Gly Trp Met Asp Phe
1               5

( 2 ) INFORMATION FOR SEQ ID NO:28:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:28:

Lys Trp Met Asp Phe
1               5

( 2 ) INFORMATION FOR SEQ ID NO:29:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:29:

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val

```
                    20                  25                  30

Gly  Ser  Asn  Thr  Tyr
               35
```

( 2 ) INFORMATION FOR SEQ ID NO:30:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:30:

```
Lys  Cys  Asn  Thr  Ala  Thr  Cys  Ala  Thr  Gln  Lys  Leu  Ala  Asn  Phe  Leu
 1                  5                       10                      15

Val  His  Ser  Ser  Asn  Asn  Phe  Gly  Pro  Ile  Leu  Pro  Pro  Thr  Asn  Val
               20                       25                      30

Gly  Ser  Asn  Thr  Tyr
               35
```

( 2 ) INFORMATION FOR SEQ ID NO:31:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:31:

```
Cys  Ser  Asn  Leu  Ser  Thr  Cys  Val  Leu  Gly  Lys  Leu  Ser  Gln  Glu  Leu
 1                  5                       10                      15

His  Lys  Leu  Gln  Thr  Tyr  Pro  Arg  Thr  Asn  Thr  Gly  Ser  Gly  Thr  Pro
               20                       25                      30
```

( 2 ) INFORMATION FOR SEQ ID NO:32:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:32:

Asp Xaa Met Gly Trp Met Asp Phe
1               5

( 2 ) INFORMATION FOR SEQ ID NO:33:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:33:

Asp Tyr Met Gly Trp Met Asp Phe
1               5

( 2 ) INFORMATION FOR SEQ ID NO:34:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:34:

Met Gly Trp Met Asp Phe
1               5

( 2 ) INFORMATION FOR SEQ ID NO:35:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:35:

Gly Trp Met Asp Phe
1               5

( 2 ) INFORMATION FOR SEQ ID NO:36:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:36:

Trp Met Asp Phe
1

( 2 ) INFORMATION FOR SEQ ID NO:37:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:37:

Lys Asp Xaa Met Gly Trp Met Asp Phe
1               5

( 2 ) INFORMATION FOR SEQ ID NO:38:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:38:

Lys Asp Tyr Met Gly Trp Met Asp Phe
1               5

( 2 ) INFORMATION FOR SEQ ID NO:39:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i i ) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:39:

Lys Met Gly Trp Met Asp Phe
1               5

(2) INFORMATION FOR SEQ ID NO:40:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:40:

Lys Gly Trp Met Asp Phe
1           5

(2) INFORMATION FOR SEQ ID NO:41:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:41:

Lys Trp Met Asp Phe
1             5

(2) INFORMATION FOR SEQ ID NO:42:

(i) SEQUENCE CHARACTERISTICS:
    (A) LENGTH: 37 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

( x i ) SEQUENCE DESCRIPTION: SEQ ID NO:42:

Lys Cys Asn Thr Ala Thr Cys Ala Thr Gln Arg Leu Ala Asn Glu Leu
1               5                   10                  15

Val His Ser Ser Asn Asn Phe Gly Pro Ile Leu Pro Pro Thr Asn Val
                20                  25                  30

Gly Ser Asn Thr Tyr
                35

( 2 ) INFORMATION FOR SEQ ID NO:43:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:43:

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
                20                  25                  30

( 2 ) INFORMATION FOR SEQ ID NO:44:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:44:

Asp Xaa Met Gly Trp Met Asp Phe
1               5

( 2 ) INFORMATION FOR SEQ ID NO:45:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:45:

Asp Tyr Met Gly Trp Met Asp Phe
1               5

( 2 ) INFORMATION FOR SEQ ID NO:46:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:46:

Met Gly Trp Met Asp Phe
1               5

( 2 ) INFORMATION FOR SEQ ID NO:47:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:47:

Gly Trp Met Asp Phe
1               5

( 2 ) INFORMATION FOR SEQ ID NO:48:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:48:

Trp Met Asp Phe
1

( 2 ) INFORMATION FOR SEQ ID NO:49:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:49:

Asn Thr Ala Thr
1

( 2 ) INFORMATION FOR SEQ ID NO:50:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:50:

Gly Thr Ala Thr
1

( 2 ) INFORMATION FOR SEQ ID NO:51:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:51:

Asn Thr Val Thr
1

( 2 ) INFORMATION FOR SEQ ID NO:52:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:52:

Asn Met Ala Thr
1

( 2 ) INFORMATION FOR SEQ ID NO:53:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:53:

Ser Asn Leu Ser Thr
1                   5

( 2 ) INFORMATION FOR SEQ ID NO:54:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:54:

Ala Ser Leu Ser Thr
1                   5

( 2 ) INFORMATION FOR SEQ ID NO:55:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:55:

Gly Asn Leu Ser Thr
1               5

( 2 ) INFORMATION FOR SEQ ID NO:56:

( i ) SEQUENCE CHARACTERISTICS:
　　　　　　　( A ) LENGTH: 11 amino acids
　　　　　　　( B ) TYPE: amino acid
　　　　　　　( C ) STRANDEDNESS: single
　　　　　　　( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:56:

Ala Thr Gln Arg Leu Ala Asn Phe Leu Val His
1               5                   10

( 2 ) INFORMATION FOR SEQ ID NO:57:

( i ) SEQUENCE CHARACTERISTICS:
　　　　　　　( A ) LENGTH: 11 amino acids
　　　　　　　( B ) TYPE: amino acid
　　　　　　　( C ) STRANDEDNESS: single
　　　　　　　( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:57:

Val Leu Gly Lys Leu Ser Gln Glu Leu His Lys
1               5                   10

( 2 ) INFORMATION FOR SEQ ID NO:58:

( i ) SEQUENCE CHARACTERISTICS:
　　　　　　　( A ) LENGTH: 11 amino acids
　　　　　　　( B ) TYPE: amino acid
　　　　　　　( C ) STRANDEDNESS: single
　　　　　　　( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:58:

Ser Ser Asn Asn Phe Gly Pro Ile Leu Pro Pro
1               5                   10

( 2 ) INFORMATION FOR SEQ ID NO:59:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:59:

Leu Gln Thr Tyr Pro Arg
1               5

( 2 ) INFORMATION FOR SEQ ID NO:60:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:60:

Asp Tyr Met Gly Trp Met Asp Phe
1               5

( 2 ) INFORMATION FOR SEQ ID NO:61:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:61:

Thr Asn Thr Gly Trp Met Asp Phe
1               5

( 2 ) INFORMATION FOR SEQ ID NO:62:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:62:

Thr Asn Val Gly Trp Met Asp Phe
1               5

(2) INFORMATION FOR SEQ ID NO:63:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:63:

Thr Asn Thr Gly Trp Leu Asp Phe
1               5

(2) INFORMATION FOR SEQ ID NO:64:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:64:

Thr Asn Val Gly Trp Leu Asp Phe
1               5

(2) INFORMATION FOR SEQ ID NO:65:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal ( v i ) ORIGINAL SOURCE:

( x i ) SEQUENCE DESCRIPTION: SEQ ID NO:65:

Thr Asn Thr Gly Ser Asn Asp Phe
1               5

( 2 ) INFORMATION FOR SEQ ID NO:66:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:66:

Thr Asn Val Gly Ser Asn Asp Phe
1               5

( 2 ) INFORMATION FOR SEQ ID NO:67:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:67:

Thr Asn Thr Gly Ser Asn Asp Tyr
1               5

( 2 ) INFORMATION FOR SEQ ID NO:68:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:68:

Thr Asn Val Gly Ser Asn Asp Tyr
1               5

( 2 ) INFORMATION FOR SEQ ID NO:69:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:69:

```
Lys Cys Asn Thr Ala Thr Cys Ala Thr Gln Arg Leu Ala Asn Phe Leu
 1               5                  10                  15
Val His Ser Ser Asn Asn Phe Gly Pro Ile Leu Pro Pro Asp Tyr Met
                20                  25                  30
Gly Trp Met Asp Phe
                35
```

( 2 ) INFORMATION FOR SEQ ID NO:70:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:70:

```
Cys Ser Asn Leu Ser Thr Cys Val Leu Gly Lys Leu Ser Gln Glu Leu
 1               5                  10                  15
His Lys Leu Gln Thr Tyr Pro Arg Asp Tyr Met Gly Trp Met Asp Phe
                20                  25                  30
```

( 2 ) INFORMATION FOR SEQ ID NO:71:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:71:

```
Lys Cys Asn Thr Ala Thr Cys Ala Thr Gln Arg Leu Ala Asn Phe Leu
 1               5                  10                  15
```

-continued

```
Val His Ser Ser Asn Asn Phe Gly Pro Ile Leu Pro Pro Thr Asn Thr
             20                  25                  30

Gly Trp Met Asp Phe
         35
```

( 2 ) INFORMATION FOR SEQ ID NO:72:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:72:

```
Cys Ser Asn Leu Ser Thr Cys Val Leu Gly Lys Leu Ser Gln Glu Leu
 1               5                  10                  15

His Lys Leu Gln Thr Tyr Pro Arg Thr Asn Thr Gly Trp Met Asp Phe
             20                  25                  30
```

( 2 ) INFORMATION FOR SEQ ID NO:73:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:73:

```
Lys Cys Asn Thr Ala Thr Cys Ala Thr Gln Arg Leu Ala Asn Phe Leu
 1               5                  10                  15

Val His Ser Ser Asn Asn Phe Gly Pro Ile Leu Pro Pro Thr Asn Thr
             20                  25                  30

Gly Trp Leu Asp Phe
         35
```

( 2 ) INFORMATION FOR SEQ ID NO:74:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (v i) ORIGINAL SOURCE:

(x i) SEQUENCE DESCRIPTION: SEQ ID NO:74:

Cys Ser Asn Leu Ser Thr Cys Val Leu Gly Lys Leu Ser Gln Glu Leu
1               5                   10                  15
His Lys Leu Gln Thr Tyr Pro Arg Thr Asn Thr Gly Trp Leu Asp Phe
                20              25                  30

(2) INFORMATION FOR SEQ ID NO:75:

(i) SEQUENCE CHARACTERISTICS:
      (A) LENGTH: 37 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:75:

Lys Cys Asn Thr Ala Thr Cys Ala Thr Gln Arg Leu Ala Asn Phe Leu
1               5                   10                  15
Val His Ser Ser Asn Asn Phe Gly Pro Ile Leu Pro Pro Thr Asn Val
                20              25                  30
Gly Ser Asn Asp Phe
                35

(2) INFORMATION FOR SEQ ID NO:76:

(i) SEQUENCE CHARACTERISTICS:
      (A) LENGTH: 32 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:76:

Cys Ser Asn Leu Ser Thr Cys Val Leu Gly Lys Leu Ser Gln Glu Leu
1               5                   10                  15
His Lys Leu Gln Thr Tyr Pro Arg Thr Asn Val Gly Ser Asn Asp Phe
                20              25                  30

(2) INFORMATION FOR SEQ ID NO:77:

(i) SEQUENCE CHARACTERISTICS:
      (A) LENGTH: 37 amino acids
      (B) TYPE: amino acid
      (C) STRANDEDNESS: single
      (D) TOPOLOGY: linear (ii) MOLECULE TYPE: peptide (iii) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:77:

```
Lys Cys Asn Thr Ala Thr Cys Ala Thr Gln Arg Leu Ala Asn Phe Leu
 1               5                   10                  15
Val His Ser Ser Asn Asn Phe Gly Pro Ile Leu Pro Pro Thr Asn Val
                20                  25                  30
Gly Ser Asn Asp Tyr
            35
```

( 2 ) INFORMATION FOR SEQ ID NO:78:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:78:

```
Cys Ser Asn Leu Ser Thr Cys Val Leu Gly Lys Leu Ser Gln Glu Leu
 1               5                   10                  15
His Lys Leu Gln Thr Tyr Pro Arg Thr Asn Val Gly Ser Asn Asp Tyr
                20                  25                  30
```

( 2 ) INFORMATION FOR SEQ ID NO:79:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:79:

```
Cys Asn Thr Ala Thr Cys Ala Thr Gln Arg Leu Ala Asn Phe Leu Val
 1               5                   10                  15
His Ser Ser Asn Asn Phe Gly Ala Ile Leu Ser Ser Thr Asn Val Gly
                20                  25                  30
Ser Asn Thr Tyr
            35
```

( 2 ) INFORMATION FOR SEQ ID NO:80:

( i ) SEQUENCE CHARACTERISTICS:
        ( A ) LENGTH: 37 amino acids
        ( B ) TYPE: amino acid ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:80:

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
            35

( 2 ) INFORMATION FOR SEQ ID NO:81:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:81:

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
            35

( 2 ) INFORMATION FOR SEQ ID NO:82:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:82:

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
            20                  25                  30

Gly Ser Asn Thr Tyr
        35

( 2 ) INFORMATION FOR SEQ ID NO:83:

( i ) SEQUENCE CHARACTERISTICS:
    ( A ) LENGTH: 36 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:83:

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Ser Thr Asn Val Gly
            20                  25                  30

Ser Asn Thr Tyr
        35

( 2 ) INFORMATION FOR SEQ ID NO:84:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:84:

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
        35

( 2 ) INFORMATION FOR SEQ ID NO:85:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:85:

Lys Cys Asn Thr Ala Thr Cys Ala Thr Gln Arg Leu Ala Asn Phe Leu
1               5                   10                  15
Val Arg Ser Ser Asn Asn Phe Gly Pro Pro Pro Pro Thr Asn Val
            20                  25                  30
Gly Ser Asn Thr Tyr
            35

( 2 ) INFORMATION FOR SEQ ID NO:86:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:86:

Cys Asn Thr Ala Thr Cys Ala Thr Gln Arg Leu Ala Asn Phe Leu Val
1               5                   10                  15
Arg Ser Ser Asn Asn Phe Gly Pro Ile Leu Pro Pro Thr Asn Val Gly
            20                  25                  30
Ser Asn Thr Tyr
        35

( 2 ) INFORMATION FOR SEQ ID NO:87:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:87:

Lys Cys Asn Thr Ala Thr Cys Ala Thr Gln Arg Leu Ala Asn Phe Leu
1               5                   10                  15
Val His Ser Ser Asn Asn Phe Gly Pro Ile Leu Pro Pro Thr Asn Val
            20                  25                  30
Gly Ser Asn Thr Tyr
            35

( 2 ) INFORMATION FOR SEQ ID NO:88:

( i ) SEQUENCE CHARACTERISTICS:
        ( A ) LENGTH: 36 amino acids
        ( B ) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:88:

```
Cys Asn Thr Ala Thr Cys Ala Thr Gln Arg Leu Ala Asn Phe Leu Val
 1               5                  10                  15
His Ser Ser Asn Asn Phe Gly Pro Ile Leu Pro Pro Thr Asn Val Gly
             20                  25                  30
Ser Asn Thr Tyr
         35
```

( 2 ) INFORMATION FOR SEQ ID NO:89:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:89:

```
Lys Cys Asn Thr Ala Thr Cys Ala Thr Gln Arg Leu Ala Asn Phe Leu
 1               5                  10                  15
Val His Ser Ser Asn Asn Phe Gly Pro Val Leu Pro Ser Thr Asn Val
             20                  25                  30
Gly Ser Asn Thr Tyr
         35
```

( 2 ) INFORMATION FOR SEQ ID NO:90:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:90:

```
Lys Cys Asn Thr Ala Thr Cys Ala Thr Gln Arg Leu Ala Asn Phe Leu
 1               5                  10                  15
Val His Ser Ser Asn Asn Leu Gly Pro Val Leu Pro Pro Thr Asn Val
             20                  25                  30
```

Gly Ser Asn Thr Tyr
            35

(2) INFORMATION FOR SEQ ID NO:91:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:91:

Lys Cys Asn Thr Ala Thr Cys Ala Thr Gln Arg Leu Ala Asn Phe Leu
 1               5                  10                 15

Val His Ser Ser Asn Asn Leu Gly Pro Val Leu Pro Ser Thr Asn Val
             20                 25                 30

Gly Ser Asn Thr Tyr
            35

(2) INFORMATION FOR SEQ ID NO:92:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:92:

Cys Asn Thr Ala Thr Cys Ala Thr Gln Arg Leu Ala Asn Phe Leu Val
 1               5                  10                 15

His Ser Ser Asn Asn Leu Gly Pro Val Leu Pro Ser Thr Asn Val Gly
             20                 25                 30

Ser Asn Thr Tyr
            35

(2) INFORMATION FOR SEQ ID NO:93:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal ( v i ) ORIGINAL SOURCE:

( x i ) SEQUENCE DESCRIPTION: SEQ ID NO:93:

Lys Cys Asn Thr Ala Thr Cys Ala Thr Gln Arg Leu Ala Asn Phe Leu
1               5                   10                  15
Val Arg Ser Ser Asn Asn Leu Gly Pro Val Leu Pro Ser Thr Asn Val
            20                  25                  30
Gly Ser Asn Thr Tyr
            35

( 2 ) INFORMATION FOR SEQ ID NO:94:

( i ) SEQUENCE CHARACTERISTICS:
      ( A ) LENGTH: 37 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:94:

Lys Cys Asn Thr Ala Thr Cys Ala Thr Gln Arg Leu Ala Asn Phe Leu
1               5                   10                  15
Val Arg Ser Ser Asn Asn Leu Gly Pro Ile Leu Pro Pro Thr Asn Val
            20                  25                  30
Gly Ser Asn Thr Tyr
            35

( 2 ) INFORMATION FOR SEQ ID NO:95:

( i ) SEQUENCE CHARACTERISTICS:
      ( A ) LENGTH: 37 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:95:

Lys Cys Asn Thr Ala Thr Cys Ala Thr Gln Arg Leu Ala Asn Phe Leu
1               5                   10                  15
Val Arg Ser Ser Asn Asn Leu Gly Pro Ile Leu Pro Ser Thr Asn Val
            20                  25                  30
Gly Ser Asn Thr Tyr
            35

( 2 ) INFORMATION FOR SEQ ID NO:96:

( i ) SEQUENCE CHARACTERISTICS:
      ( A ) LENGTH: 37 amino acids
      ( B ) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:96:

```
Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
                20                  25                  30

Gly Ser Asn Thr Tyr
                35
```

( 2 ) INFORMATION FOR SEQ ID NO:97:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:97:

```
Lys Cys Asn Thr Ala Thr Cys Ala Thr Gln Arg Leu Ala Asn Phe Leu
1               5                   10                  15

Ile His Ser Ser Asn Asn Phe Gly Pro Ile Leu Pro Pro Thr Asn Val
                20                  25                  30

Gly Ser Asn Thr Tyr
                35
```

( 2 ) INFORMATION FOR SEQ ID NO:98:

( i ) SEQUENCE CHARACTERISTICS:
( A ) LENGTH: 36 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:98:

```
Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
                20                  25                  30
```

Ser Asn Thr Tyr
         35

( 2 ) INFORMATION FOR SEQ ID NO:99:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:99:

Lys Cys Asn Thr Ala Thr Cys Ala Thr Gln Arg Leu Ala Asn Phe Leu
 1               5                  10                  15
Ile Arg Ser Ser Asn Asn Leu Gly Ala Ile Leu Ser Ser Thr Asn Val
             20                  25                  30
Gly Ser Asn Thr Tyr
         35

( 2 ) INFORMATION FOR SEQ ID NO:100:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:100:

Lys Cys Asn Thr Ala Thr Cys Ala Thr Gln Arg Leu Ala Asn Phe Leu
 1               5                  10                  15
Ile Arg Ser Ser Asn Asn Leu Gly Ala Val Leu Ser Pro Thr Asn Val
             20                  25                  30
Gly Ser Asn Thr Tyr
         35

( 2 ) INFORMATION FOR SEQ ID NO:101:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (v i) ORIGINAL SOURCE:

(x i) SEQUENCE DESCRIPTION: SEQ ID NO:101:

```
Lys Cys Asn Thr Ala Thr Cys Ala Thr Gln Arg Leu Ala Asn Phe Leu
 1               5                   10                  15
Ile Arg Ser Ser Asn Asn Leu Gly Pro Val Leu Pro Pro Thr Asn Val
                20              25                  30
Gly Ser Asn Thr Tyr
            35
```

(2) INFORMATION FOR SEQ ID NO:102:

(i) SEQUENCE CHARACTERISTICS:
        (A) LENGTH: 37 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:102:

```
Lys Cys Asn Thr Ala Thr Cys Ala Thr Gln Arg Leu Thr Asn Phe Leu
 1               5                   10                  15
Val His Ser Ser His Asn Leu Gly Ala Ala Leu Leu Pro Thr Asp Val
                20              25                  30
Gly Ser Asn Thr Tyr
            35
```

(2) INFORMATION FOR SEQ ID NO:103:

(i) SEQUENCE CHARACTERISTICS:
        (A) LENGTH: 37 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:

(x i) SEQUENCE DESCRIPTION: SEQ ID NO:103:

```
Lys Cys Asn Thr Ala Thr Cys Ala Thr Gln Arg Leu Thr Asn Phe Leu
 1               5                   10                  15
Val His Ser Ser His Asn Leu Gly Ala Ala Leu Ser Pro Thr Asp Val
                20              25                  30
Gly Ser Asn Thr Tyr
            35
```

(2) INFORMATION FOR SEQ ID NO:104:

(i) SEQUENCE CHARACTERISTICS:
        (A) LENGTH: 36 amino acids
        (B) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:104:

Cys Asn Thr Ala Thr Cys Ala Thr Gln Arg Leu Thr Asn Phe Leu Val
1               5                   10                  15

His Ser Ser His Asn Leu Gly Ala Ala Leu Pro Ser Thr Asp Val Gly
            20                  25                  30

Ser Asn Thr Tyr
        35

( 2 ) INFORMATION FOR SEQ ID NO:105:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:105:

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35

( 2 ) INFORMATION FOR SEQ ID NO:106:

( i ) SEQUENCE CHARACTERISTICS:
( A ) LENGTH: 37 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:106:

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30

```
Gly Ser Asn Thr Tyr
         35
```

( 2 ) INFORMATION FOR SEQ ID NO:107:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:107:

```
Lys Cys Asn Thr Ala Thr Cys Ala Thr Gln Arg Leu Thr Asn Phe Leu
 1               5                   10                      15

Val Arg Ser Ser His Asn Leu Gly Pro Ala Leu Pro Pro Thr Asp Val
         20                  25                  30

Gly Ser Asn Thr Tyr
         35
```

( 2 ) INFORMATION FOR SEQ ID NO:108:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:108:

```
Asp Tyr Xaa Met Gly Trp Met Asp Phe
 1               5
```

APPETITE REGULATING COMPOSITIONS

FIELD OF THE INVENTION

The field of the invention is biology and, more particularly, the biology of control of food intake, appetite and satiation, and control of body weight. The invention relates to compositions which comprise an amylin agonist and a cholecystokinin ("CCK") agonist, or various hybrid compositions described herein, and their use in the suppression of food intake. The invention also relates to methods for controlling food intake, appetite and satiation, and methods for controlling body weight.

BACKGROUND

Publications and other materials including patents and patent applications used to illuminate the specification are hereby incorporated in their entireties by reference. Obesity is becoming increasingly prevalent in developed societies. For example, approximately 30% of adults in the U.S. were estimated to be 20 percent above desirable body weight—an accepted measure of obesity sufficient to impact a health risk ("Harrison's Principles of Internal Medicine 12th Edition," McGraw Hill, inc. (1991) p. 411). In these individuals, obesity may be a contributing factor to increased incidence of cardiovascular disease, hypertension, hypercholesterolemia, Type II diabetes mellitus (also referred to as non-insulin dependent diabetes mellitus) and certain cancers. Kolata, *Science* 227:1019–1020 (1985). For example, hypertension, obesity and glucose intolerance (impaired glucose tolerance and Type 2 diabetes mellitus) are associated in both clinical and epidemiological studies (Chiang et al., *Circulation* 39:403–421 (1960); Sims, *Hypertension* 4(Suppl. 3):43–49 (1982); Bray, *Dis. Mon.* 26:1–85 (1979); West, *Epidemiology of Diabetes and its Vascular Lesions*, Elsevier/North Holland, New York, pp. 191–284, 351–389 (1978); Medalie et al., *Arch. Int. Med.* 135:811–817 (1975); Zimmett, *Diabetologia* 22:399–411 (1982); Barrett-Connor, *Am. J. Epidemiol.* 113:276–284 (1981); Jarrett et al., *Int. J. Epidemiol.* 7:15–24 (1978); Butler et al., *Am. J. Epidemiol.* 16:971–980 (1982)), and may have common pathogenetic mechanisms (Modan et al., *J. Clin. Invest.* 75:809–817 (1985)). Weight reduction is often recommended as the first course of action for patients suffering from Type II diabetes mellitus, hypertension, hypercholesterolemia, coronary artery heart disease, gout and osteoarthritis.

However, there are relatively few therapeutic tools which can be employed by a physician to accomplish weight loss in patients. Pharmaceutical agents currently in use are effective for short term therapy, but may be unacceptable for long-term use due to the possible development of tolerance and possibly undesirable side effects. Agents which, at relatively low doses, reduce food intake by mimicking the body's own satiety signals would be of greater advantage than currently available weight loss agents for use in chronic therapy, having a more desirable side effect profile than those currently available.

CCK

CCK was reportedly identified in 1928 from preparations of intestinal extracts by its ability to stimulate gallbladder contraction. Other biological actions of CCK have since been reported, including stimulation of pancreatic secretion, delayed gastric emptying, stimulation of intestinal motility and stimulation of insulin secretion. See Lieverse et al., *Ann. N.Y. Acad. Sci.* 713: 268–272 (1994). The actions of CCK, also reportedly include effects on cardiovascular function, respiratory function, neurotoxicity and seizures, cancer cell proliferation, analgesia, sleep, sexual and reproductive behaviors, memory, anxiety and dopamine-mediated behaviors. Crawley and Corwin, *Peptides* 15: 731–755 (1994). Other reported effects of CCK include stimulation of pancreatic growth, stimulation of gallbladder contraction, inhibition of gastric acid secretion, pancreatic polypeptide release and a contractile component of peristalsis. Additional reported effects of CCK include vasodilation. Walsh, "Gastrointestinal Hormones," *In Physiology of the Gastrointestinal Tract* (3d ed. 1994; Raven Press, New York).

It has been reported that injections of combinations of glucagon, CCK and bombesin potentiated the inhibition of intake of condensed milk test meals in nondeprived rats over the inhibitions observed with individual compounds. Hinton et al., *Brain Res. Bull.* 17:615–619 (1986). It has also been reported that glucagon and CCK synergistically inhibit sham feeding in rats. LeSauter and Geary, *Am. J. Physiol.* 253:R217–225 (1987); Smith and Gibbs, *Annals N.Y. Acad. Sci.* 713:236–241 (1994). It has also been suggested that estradiol and CCK can have a synergistic effect on satiety. Dulawa et al., *Peptides* 15:913–918 (1994); Smith and Gibbs, supra. It has also been proposed that signals arising from the small intestine in response to nutrients therein may interact synergistically with CCK to reduce food intake. Cox, *Behav. Brain Res.* 38:35–44 (1990). Additionally, it has been reported that CCK induces satiety in several species. For example, it has been reported that feeding depression was caused by CCK injected intraperitoneally in rats, intraarterially in pigs, intravenously in cats and pigs, into the cerebral ventricles in monkeys, rats, dogs and sheep, and intravenously in obese and nonobese humans. See Lieverse et al., supra. Studies from several laboratories have reportedly confirmed the behavioral specificity of low doses of CCK on inhibition in feeding, by comparing responding for food to responding for nonfood reinforcers in both monkeys and rats and by showing that CCK elicits the sequence of behaviors normally observed after meal ingestion (i.e., the postprandial satiety sequence). Additionally, comparison of behavior after CCK to behavior after food ingestion, alone or in combination with CCK has reportedly revealed behavioral similarities between CCK and food ingestion. Crawley and Corwin, supra. It has also been reported that CCK in physiological plasma concentrations inhibits food intake and increases satiety in both lean and obese humans. See Lieverse et al., supra.

CCK was characterized in 1966 as a 33-amino acid peptide. Crawley and Corwin, supra. Human CCK-33 has the following amino acid sequence:

Lys—Ala—Pro—Ser—Gly—Arg—Met—Ser—Ile—Val—Lys—
Asn—Leu—Gln—Asn—Leu—Asp—Pro—Ser—His—Arg—Ile—
Ser—Asp—Arg—Asp—Tyr—(SO$_3$H)—Met—Gly—Trp—Met—
Asp—Phe—NH$_2$    [SEQ ID NO. 1]

Species-specific molecular variants of the amino acid sequence of CCK have been identified. The 33-amino acid sequence and a truncated peptide, its 8-amino acid C-terminal sequence (CCK-8) have been reportedly identified in pig, rat, chicken, chinchilla, dog and humans. A 39-amino acid sequence was reportedly found in pig, dog and guinea pig. A 58-amino acid sequence was reported to have been found in cat, dog and humans. Frog and turtle reportedly show 47-amino acid sequences homologous to both CCK and gastrin. Very fresh human intestine has been reported to contain small amounts of an even larger molecule, termed CCK-83. In the rat, a principal intermediate form has been reportedly identified, and is termed CCK-22. Walsh, "Gastrointestinal Hormones," In *Physiology of the Gastrointestinal Tract* (3d ed. 1994; Raven Press, New York). A nonsulfated CCK-8 and a tetrapeptide (termed CCK-4 (CCK30-33)) have been reported in rat brain. The C-terminal penta peptide (termed CCK-4 (CCK 29-33)) conserves the structural homology of CCK, and also homology with the neuropeptide, gastrin. The C-terminal sulfated octapeptide sequence, CCK-8, Asp-Tyr($SO_3$H)-Met-Gly-Trp-Met-Asp-Phe-$NH_2$ [SEQ. ID NO. 2], is reportedly relatively conserved across species. Cloning and sequence analysis of a cDNA encoding preprocholecystokinin from rat thyroid carcinoma, porcine brain, and porcine intestine reportedly revealed 345 nucleotides coding for a precursor to CCK, which is 115 amino acids and contains all of the CCK sequences previously reported to have been isolated. Crawley and Corwin, supra.

CCK is said to be distributed throughout the central nervous system and in endocrine cells and enteric nerves of the upper small intestine. CCK agonists include CCK itself (also referred to as CCK-33), CCK-8 (CCK26-33), non-sulfated CCK-8, pentagastrin (CCK-5 or CCK(29-33)), and the tetrapeptide, CCK-4 (CCK30-33). At the pancreatic CCK receptor, CCK-8 reportedly displaced binding with a 1000-5000 greater potency than unsulfated CCK-8 or CCK-4, and CCK-8 has been reported to be approximately 1000-fold more potent than unsulfated CCK-8 or CCK-4 in stimulating pancreatic amylase secretion. Crawley and Corwin, supra. In homogenates from the cerebral cortex, CCK receptor binding was said to be displaced by unsulfated CCK-8 and by CCK-4 at concentrations that were equimolar, 10-fold or 100-fold greater than sulfated CCK-8. Id.

Receptors for CCK have been reportedly identified in a variety of tissues, and two primary subtypes have been described: type A receptors and type B receptors. Type A receptors have been reported in peripheral tissues including pancreas, gallbladder, pyloric sphincter and afferent vagal fibers, and in discrete areas of the brain. The type A receptor subtype ($CCK_A$) has been reported to be selective for the sulfated octapeptide. The Type B receptor subtype ($CCK_B$) has been identified throughout the brain and in the stomach, and reportedly does not require sulfation or all eight amino acids. See Reidelberger, *J. Nutr.* 124 (8 Suppl.) 1327S-1333S (1994); Crawley and Corwin, supra. $CCK_A$ agonists also include A-71623 and A-708874, which were developed based on the structure of CCK-4. Members of another series of $CCK_A$ agonists, which includes JMV-180, are reportedly active in stimulating pancreatic amylase release and inhibiting feeding. Crawley and Corwin, supra. Examples of non-peptide $CCK_A$ agonists are L-364718 and FPL 15849KF. Crawley and Corwin, supra. Morley et al., *Am. J. Physiol.* 267:R178-R184 (1994). $CCK_B$ agonists include CCK-8, unsulfated CCK-8, CCK-4, and BC 264 (which is a peptidase-resistant CCK derivative). Crawley and Corwin, supra.

Amylin

Amylin is a 37-amino acid protein hormone. The structure of human amylin is as follows:

Lys—Cys—Asn—Thr—Ala—Thr—Cys—Ala—Thr—Gln—Arg—
Leu—Ala—Asn—Phe—Leu—Val—His—Ser—Ser—Asn—Asn—
Phe—Gly—Ala—Ile—Leu—Ser—Ser—Thr—Asn—Val—Gly—
Ser—Asn—Thr—Tyr—$NH_2$  [SEQ. ID NO. 3]

It was isolated, purified and chemically characterized as the major component of amyloid deposits in the islets of pancreases of human Type II diabetics (Cooper et al., *Proc. Natl Acad. Sci., USA* 84:8628-8632 (1987)). The amylin molecule has two important post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the CLAIMS-terminal position, a typical sequence for amidation by protein amidating enzyme, PAM (Cooper et al., *Biochem. Biophys. Acta* 1014:247-258 (1989)). Amylin is the subject of United Kingdom patent application Serial No. 8709871, filed Apr. 27, 1987, and corresponding U.S. Pat. No. 5,367,052, issued Nov. 22, 1994. An overview of amylin's structure, synthesis, secretion and molecular physiology is found in Pittner et al., *J. Cell. Biochem.* 55S:19-28 (1994).

Both the chemical structure and the gene sequence of amylin have been said to support the determination that it is a biologically active or "messenger" molecule. The chemical structure is nearly 50% identical to the calcitonin-gene-related peptides (CGRP), also 37 amino acid proteins which are widespread neurotransmitters with many potent-biological actions, including vasodilation. Amylin and CGRP share the $^2$Cys-$^7$Cys disulphide bridge and the C-terminal amide, both of which are essential for full biologic activity (Cooper et al., *Proc. Natl Acad. Sci.* 85:7763-7766 (1988)).

Amylin is primarily synthesized in pancreatic beta cells and is secreted in response to nutrient stimuli such as glucose and arginine. Studies with cloned beta cell tumor lines (Moore et al., *Biochem. Biophys. Res. Commun.* 179:1-9 (1991)), isolated islets (Kanatsuka et al., *FEBS Letts.* 259:199-201 (1989)) and perfused rat pancreases (Ogawa et al., *J. Clin. Invest.* 85:973-976 (1990)) have shown that short pulses, 10 to 20 minutes, of nutrient secretogogues such as glucose and arginine, stimulate release of amylin as well as insulin. The molar amylin:insulin ratio of the secreted proteins varies between preparations from about 0.01 to 0.4, but appears not to vary much with different stimuli in any one preparation. However, during prolonged stimulation by elevated glucose, the amylin:insulin ratio can progressively increase (Gedulin et al., *Biochem. Biophys. Res. Commun.* 180:782-789 (1991)). Thus, perhaps because gene expression and rate of translation are independently controlled, amylin and insulin are not always secreted in a constant ratio.

Amylin-like immunoreactivity has been measured in circulating blood in rodents and humans by a variety of radioimmunoassays all of which use rabbit anti-amylin antiserum, and most of which use an extraction and concentration procedure to increase assay sensitivity. In normal humans, fasting amylin levels from 1 to 10 pM and post-prandial or post-glucose levels of 5 to 20 pM have been reported (e.g., Hartter et al., *Diabetologia* 34:52-54 (1991); Sanke et al., *Diabetologia* 34:129-132 (1991); Koda et al., *The Lancet* 339:1179-1180 (1992)). In obese, insulin-resistant individuals, post-food amylin levels can go higher, reaching up to about 50 pM. For comparison, the values for fasting and post-prandial insulin are 20 to 50 pM, and 100 to 300 pM respectively in healthy people, with perhaps 3-to 4-fold higher levels in insulin-resistant people. In Type 1 diabetes, where beta cells are destroyed, amylin levels are at or below the level of detection and do not rise in response to glucose (Koda et al., supra. In normal mice and rats, basal amylin levels have been reported from 30 to 100 pM, while values up to 600 pM have been measured in certain insulin-resistant, diabetic strains of rodents (e.g., Huang et al., *Hypertension* 19:1101-1109 (1991)); Gill et al., *Life Sciences* 48:703-710 (1991).

It has been discovered that certain actions of amylin are similar to known non-metabolic actions of CGRP and calcitonin; however, the metabolic actions of amylin discovered during investigations of this newly identified protein appear to reflect its primary biologic role. At least some of these metabolic actions are mimicked by CGRP, albeit at doses which are markedly vasodilatory (see, e.g., Leighton et al., *Nature* 335:632–635 (1988); Molina et al., *Diabetes* 39:260–265 (1990)).

The first discovered action of amylin was the reduction of insulin-stimulated incorporation of glucose into glycogen in rat skeletal muscle (Leighton et al., *Nature* 335:632–635 (1988)); the muscle was made "insulin-resistant". Subsequent work with rat soleus muscle has indicated that amylin reduces glycogen-synthase activity, promotes conversion of glycogen phosphorylase from the inactive b form to the active a form, promotes net loss of glycogen (in the presence or absence of insulin), increases glucose-6-phosphate levels, and can increase lactate output (see, e.g., Deems et al., *Biochem. Biophys. Res. Commun.* 181:116–120 (1991)); Young et al., *FEBS Letts.* 281:149–151 (1991)). Whether amylin interferes with glucose transport per se is uncertain (see, e.g., Young et al., *Am. J. Physiol.* 259:E457–E461 (1990); Zierath et al., *Diabetologia* 35:26–31 (1992)). Studies of amylin and insulin dose-response relations show that amylin acts as a noncompetitive or functional antagonist of insulin in skeletal muscle (Young et al., *Am. J. Physiol.* 263:E274–E281 (1992)). Thus, at an effective concentration of amylin, no concentration of insulin can overcome amylin action. There is no evidence that amylin interferes with insulin binding to its receptors, or the subsequent activation of insulin receptor tyrosine kinase (Follett et al., *Clinical Research* 39:39A (1991)); Koopmans et al., *Diabetologia* 34:218–224 (1991)).

It is believed that amylin acts through receptors present in plasma membranes. Beaumont et al., *Mol. Pharmacol.* 44:493–497 (1993). It has been reported that amylin works in skeletal muscle via a receptor-mediated mechanism that promotes glycogenolysis, by activating the rate-limiting enzyme for glycogen breakdown, phosphorylase a (Young et al., *FEBS Letts.* 281:149–151 (1991)). Studies of amylin and CGRP, and the effect of the antagonist $^{8-37}$CGRP, suggest that amylin acts via its own receptor (Wang et al., *FEBS Letts.* 219:195–198 (1991)), counter to the conclusion of other workers that amylin may act primarily at CGRP receptors (e.g., Chantry et al., *Biochem. J.* 277:139–143 (1991)); Galeazza et al., *Peptides* 12:585–591 (1991)); Zhu et al., *Biochem. Biophys. Res. Commun.* 177:771–776 (1991)). Amylin receptors and their use in various methods for screening and assaying for amylin agonist and antagonist compounds are described in U.S. Pat. No. 5,264,372, issued Nov. 23, 1993.

The biological actions of amylin relating to fuel metabolism are discussed in Young et al., *J. Cell. Biochem.* 555:12–18 (1994). While amylin has marked effects on hepatic fuel metabolism in vivo, there is no general agreement as to what amylin actions are seen in isolated hepatocytes or perfused liver. The available data do not support the idea that amylin promotes hepatic glycogenolysis, i.e., it does not act like glucagon (e.g., Stephens, et al., *Diabetes* 40:395–400 (1991)); Gomez-Foix et al., *Biochem J.* 276:607–610 (1991)). It has been suggested that amylin may act on the liver to promote conversion of lactate to glycogen and to enhance the amount of glucose able to be liberated by glucagon (see Roden et al., *Diabetologia* 35:116–120 (1992)). Thus, amylin could act as an anabolic partner to insulin in liver, in contrast to its catabolic action in muscle.

The effect of amylin on regional hemodynamic actions, including renal blood flow, in conscious rats was recently reported (Gardiner et al., *Diabetes* 40:948–951 (1991)). The authors noted that infusion of rat amylin was associated with greater renal vasodilation and less mesenteric vasoconstriction than is seen with infusion of human α-CGRP. They concluded that, by promoting renal hyperemia to a greater extent than did α-CGRP, rat amylin could cause less marked stimulation of the renin-angiotensin system, and thus, less secondary angiotensin II-mediated vasoconstriction. It was also noted, however, that during co-infusion of human α-$^{8-37}$CGRP and rat amylin, renal and mesenteric vasoconstrictions were unmasked, presumably due to unopposed vasoconstrictor effects of angiotensin II, and that this finding is similar to that seen during co-infusion of human α-CGRP and human α-$^{8-37}$CGRP (id.).

A striking effect of amylin in vivo in rodents is stimulation of a sharp rise in plasma lactate, followed by a rise in plasma glucose (Young et al., *FEBS Letts.* 281:149–151 (1991)). Evidence indicates that the increased lactate provides substrate for glucose production and that amylin actions can occur independent of changes in insulin or glucagon. In "glucose clamp" experiments, amylin infusions cause "insulin resistance", both by reducing peripheral glucose disposal, and by limiting insulin-mediated suppression of hepatic glucose output (e.g., Frontoni et al., *Diabetes* 40:568–573 (1991)); Koopmans et al., *Diabetologia* 34:218–224 (1991)).

In fat cells, contrary to its adrenalin-like action in muscle, amylin has no detectable actions on insulin-stimulated glucose uptake, incorporation of glucose into triglyceride, $CO_2$ production (Cooper et al., *Proc. Natl. Acad. Sci.* 85:7763–7766 (1988)) epinephrine-stimulated lipolysis, or insulin-inhibition of lipolysis (Lupien and Young, *Diabetes Nutrition and Metabolism— Clinical and Experimental* 6:13–18 (1993)). Amylin thus exerts tissue-specific effects, with direct action on skeletal muscle, marked indirect (via supply of substrate) and perhaps direct effects on liver, while adipocytes appear "blind" to the presence or absence of amylin. Giving regard to amylin's effects on muscle, liver and adipose tissue, it has been proposed that excess amylin is associated with obesity, and that obesity may be treated with amylin antagonists. U.S. Pat. No. 5,280,014, issued Jan. 18, 1994.

Non-metabolic actions of amylin include vasodilator effects which may be mediated by interaction with CGRP vascular receptors. Brain et al., *Eur. J. Pharmacol.* 183:2221 (1990). It has also been discovered that amylin markedly increases plasma renin activity in intact rats when given subcutaneously in a manner that avoids any disturbance of blood pressure. Methods for treating renin-related disorders with amylin antagonists are described in U.S. Pat. No. 5,376,638, issued Dec. 27, 1994.

It has been shown that amylin agonists can reduce gastric emptying (Young et al., *Diabetologia* (June 1995, in press)), which action is believed to contribute to their ability to reduce post-prandial plasma glucose levels (Moyses and Kolterman, *Drugs of the Future* (May 1995)). Methods for reducing gastric motility and slowing gastric emptying comprising the administration of an amylin agonist (including amylin) are the subject of U.S. patent application Ser. No. 08/118,381, filed Sep. 7, 1993 and U.S. patent application Ser. No. 08/302,069, filed Sep. 7, 1994.

Amylin has been reported to reduce food intake in rats and mice when administered into the brain. Balasubramaniam et al., *Peptides* 12:919–924 (1991); Chance et al., *Brain Res.* 539:352–354 (1991). An anorectic effect of amylin has been reportedly observed after intraperitoneal (IP) injection in mice and rats. Morley and Flood, *Peptides* 12:865–869 (1991); Morley et al., *Pharmacol. Biochem. Behav.* 44:577–580 (1993). It has also been reported that amylin, when administered IP in rats at a dosage of 0.5 µg/kg, significantly decreased food intake. Lutz et al., *Physiology & Behavior* 55:891–895 (1994). Reported dose-dependent side effects of injected amylin agonist in man include nausea, vomiting, diarrhea, flushing and postural hypotension. See, e.g., Moyses and Kolterman, supra.

SUMMARY OF THE INVENTION

Applicants have discovered that amylin agonists and CCK agonists when administered together, have a synergistic effect on reduction of food intake. The present application describes the use of an amylin agonist in conjunction with a CCK agonist for the control of food intake. For example, an IP injection of 1.0 µg/kg CCK-8 or of 1.0 µg/kg rat amylin has no measurable effect on food intake. But administration of 0.1 µg/kg of each peptide causes a substantial reduction of food intake about equivalent to that seen with 100 µg/kg of either peptide alone.

In one aspect, the present invention is directed to methods and compositions for reducing food intake, controlling appetite or controlling body weight in mammals, including humans. Control of body weight resulting from controlled appetite may occur as a result, for example, of less food being taken in per meal or as a result of a longer time elapsing between meals. Such methods comprise the administration of a preferred composition for suppression of food intake. Preferred compositions include a combination of an amylin agonist and a CCK agonist. Preferred compositions also include an amylin and a CCK agonist which are co-administered.

In another aspect, the present invention is directed to compositions comprising an amylin agonist and a CCK agonist admixed in a form suitable for therapeutic administration, which compositions are useful, for example, in the claimed methods for reducing food intake, controlling appetite and/or control of body weight. By amylin agonist is meant a compound having one or more of the known biological activities of amylin, in particular, the ability to reduce food intake in a mammal including a peptide or its equivalent having similar a amino acid sequence to a known amylin (such as human amylin, rat amylin and dog amylin) or amylin agonist (such as salmon calcitonin or CGRP). The term amylin agonist includes amylins such as human amylin (h-amylin). Generally, useful amylin agonists exhibit an $EC_{50}$ of $\leq 500$ nanomoles/liter in the soleus muscle assay. Good amylin agonists have an $EC_{50}$ of $\leq 250$ nanomoles/liter. Preferred amylin agonists have an $EC_{50}$ of $\leq 100$ nanomoles/liter, but more preferably less than about 1 to 5 nM, less than 1 nM, or less than 50 pM. Preferred amylin agonists are described herein and in commonly owned U.S. patent application entitled, "Novel Amylin Agonist Peptides and Uses Therefor", filed May 30, 1995 (applicant's docket 213/080) and corresponding PCT application Publication No. WO93/10146, published May 27, 1993. Particularly preferred amylin agonists for use in the presently claimed methods and compositions include $^{25,28,29}$Pro-h-amylin, s-calcitonin and h-amylin. Other amylin agonists include compounds having additional amino acids at the N-terminal end, including [Pro-NH] amylin and [Pro,Arg-NH-] amylin.

By CCK agonist is meant a compound having one or more of the known biological activities of CCK, but at least the ability to reduce food intake in a mammal, including a peptide or its equivalent having a similar amino acid sequence to a known CCK or portion thereof. The term CCK agonist includes CCKs (such as human CCK). Preferred CCK agonists include those which act at CCK subtype A receptors. A preferred $CCK_A$ agonist is CCK-8.

By reducing food intake is meant reducing the intake of food compared to what the food intake would be in the absence of any treatment or treatment with placebo.

In such compositions, the dosage of each of said amylin agonist and said CCK agonist are preferably in amounts of between about 0.1 µg/kg/day to about 10 µg/kg/day, and more preferably, between about 0.1 µg/kg/day to about 1 µg/kg/day, where such agonists are substantially or entirely peptide structures related, respectively, to amylin, $^{25,28,29}$Pro-h-amylin, and salmon calcitonin, or CCK and CCK-8. In the case of use of non-peptide agonists in such methods, the dosages of non-peptide agonists are preferably increased (or decreased) by the ratio of potency of $^{25,28,29}$Pro-h-amylin (in the case of amylin agonists) or CCK (in the case of CCK agonists) to the potency of such non-peptide agonists.

In another aspect, the present invention is directed to methods for reducing food intake in a mammal comprising administering to the mammal an effective food intake-reducing combination of an amylin agonist and a CCK agonist.

In another aspect, the present invention is directed to methods for the control of appetite in a mammal comprising coadministering to the mammal therapeutically effective amounts of an amylin agonist and a CCK agonist.

In another aspect, the present invention is directed to methods for controlling body weight of a subject comprising administering to said subject an effective food intake-reducing amount of an amylin agonist and a CCK agonist.

In preferred embodiments of these methods, the amylin agonist is $^{25,28,29}$Pro-h-amylin, s-calcitonin or h-amylin. In other preferred embodiments of these methods, the CCK agonist is a $CCK_A$ agonist, preferably CCK-8.

In other preferred embodiments of these methods, the amount of each of the amylin agonist and the CCK agonist administered is between about 0.1 µg/kg/day and about 10 µg/kg/day, and preferably between about 0.1 µg/kg/day and about 1 µg/kg/day.

In another aspect, the present invention is directed to hybrid peptides which incorporate features of amylin agonist peptides and CCK agonist peptides, wherein such hybrid peptides feature an amylin agonist peptide covalently linked to a CCK agonist peptide. Other hybrid peptide compounds, some of which employ linkers, and which incorporate various features of amylin agonists and CCK agonists, are also provided.

In one embodiment, the hybrid peptides cleave in vivo to allow each component to act independently. In such case, in order for the hybrid peptides to be cleavable in vivo, at least one of the hetero atoms along the backbone of the linker is oxygen, providing an ester linkage. In another embodiment, the hybrid do not cleave in vivo, but remain intact. Such hybrid peptides possess both amylin agonist and CCK agonist biological activities in a single molecule. In such case, we have discovered that appreciable in vivo stability is desired, and, in order for the hybrid peptides not to be cleavable in vivo, all of the hereto atoms along the backbone of the linker provided are nitrogen, thus giving rise to amide or urea linkages.

In yet another aspect, the present invention is directed to a hybrid peptide composition comprising an amylin agonist peptide and a CCK agonist peptide covalently linked by the following structure:

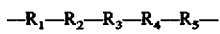

wherein said amylin agonist peptide and said CCK agonist peptide are linked via the $NH_2$ of the N-terminus of either peptide and/or via a side chain $NH_2$ of either peptide (provided that a side chain containing an $NH_2$ is present in such peptide); and (a) $R_1$ is $CONH(CH_2)N$, $COO(CH_2)n$, or $CO(CH_2)n$, where n=1–6;

(b) $R_2$ is $OCO(CH_2)_n$ (where n=1–6), $NHCO(CH_2)_n$ (where n=1–6), $OCOC_6H_4$ (ortho, meta or para linked), $COOC_6H_4$ (ortho, meta or para linked), $COOC_6H_4O$ (ortho, meta or para substituted), $NHCOC_6H_4$ (ortho, meta or para linked), $NHCOC_6H_4O$ (ortho, meta or para substituted), $CONHC_6H_4NH$ (ortho, meta or para substituted), O—X (where X is any amino acid linked via its carboxyl group, and NH—X (where X is any amino acid liked via its carboxyl group);

(c) $R_3$ is $CH_2$, $CF_2$, CO, CS or CNH;

(d) $R_4$ is O or NH; and (e) $R_5$ is $(CH_2)_nNHCO$, $(CH_2)_nOCO$, $(CH_2)_nCO$, where n=1–6;

In another aspect, the present invention is directed to a hybrid peptide composition comprising an amylin agonist peptide and a CCK agonist peptide covalently linked by the following structure:

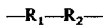

wherein said amylin agonist peptide and said CCK agonist peptide are linked via the $NH_2$ of the N-terminus of either peptide and a side chain $NH_2$ of either peptide (provided that a side chain containing an $NH_2$ is present in such peptide); and (a) $R_1$ is $CONH(CH_2)_n$, $COO(CH_2)N$, or $CO(CH_2)N$; and (b) $R_2$ is $(CH_2)_nNHCO$, $(CH_2)_nOCO$, $(CH_2)_nCO$, where n=1–6.

Preferred hybrid peptides of this sort include hybrid peptides which incorporate as the amylin agonist peptide: KCNTATCATQRLANFLVHSSNNFGPILPPTNVGSNTY-$NH_2$, [SEQ. ID. NO. 4] wherein the cysteine residues at positions 2 and 7 are linked by a disulfide linkage, the amylin agonist peptide, KCNTATCATQKLANFLVHSSNNFGPILPPTNVGSNTY-NH2, [SEQ. ID. NO. 5] wherein the cysteine residues at positions 2 and 7 are linked by a disulfide linkage, or the amylin agonist peptide, CSNLSTCVLGKLSQELHKLQTYPRTNTGSGTP-$NH_2$, [SEQ. ID. NO. 6] wherein the cysteine residues at positions 1 and 7 are linked by a disulfide linkage.

Preferred hybrid peptides of this sort also include hybrid peptides which incorporate as the CCK agonist peptide:

$DY(OSO_3H)MGWMDF-NH_2$, [SEQ. ID. NO. 7] $DYMGWMDF-NH_2$, [SEQ. ID. NO. 8] $MGWMDF-NH_2$, [SEQ. ID. NO. 9] $GWMDF-NH_2$ [SEQ. ID. NO. 10], $WMDF-NH_2$ [SEQ. ID. NO. 11], $KDY(OSO_3H)MGWMDF-NH_2$ [SEQ. ID. NO. 12], $KDYMGWMDF-NH_2$ [SEQ. ID. NO. 13], $KMGWMDF-NH_2$ [SEQ. ID. NO. 14], $KGWMDF-NH_2$ [SEQ. ID. NO. 15], or $KWMDF-NH_2$ [SEQ. ID. NO. 16].

In another aspect, the present invention is directed to a hybrid peptide composition comprising an amylin agonist peptide and a CCK agonist peptide covalently linked by the following structure:

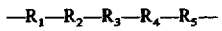

wherein said amylin agonist peptide and said CCK agonist peptide are linked via the side chain carboxylic acid group of either peptide (provided that a side chain containing an carboxylic acid group is present in such peptide) to $R_1$, and via the $NH_2$ of the N-terminus or a side chain $NH_2$ of either peptide (provided that a side chain containing $NH_2$ is present in such peptide) to $R_5$; and (a) $R_1$ is $NH(CH_2)_n$ or $O(CH_2)n$, where n=1–6;

(b) $R_2$ is $OCO(CH_2)_n$ (where n=1–6), $NHCO(CH_2)_n$ (where n=1–6), $OCOC_6H_4$ (ortho, meta or para linked), $COOC_6H_4$ (ortho, meta or para linked), $COOC_6H_4O$ (ortho, meta or para substituted), $NHCOC_6H_4$ (ortho, meta or para linked), $NHCOC_6H_4O$ (ortho, meta or para substituted), $CONHC_6H_4NH$ (ortho, meta or para substituted), O—X (where X is any amino acid linked via its carboxyl group, and NH—X (where X is any amino acid liked via its carboxyl group);

(c) $R_3$ is $CH_2$, $CF_2$, CO, CS or CNH;

(d) $R_4$ is O or NH; and (e) $R_5$ is $(CH_2)_nNHCO$, $(CH_2)_nOCO$, $(CH_2)_nCO$, where n=1–6;

In still another aspect, the present invention is directed to a hybrid peptide composition comprising an amylin agonist peptide and a CCK agonist peptide covalently linked by the following structure:

wherein said amylin agonist peptide and said CCK agonist peptide are linked via the side chain carboxylic acid group of either peptide (provided that a side chain containing an carboxylic acid group is present in such peptide) to $R_1$, and via the $NH_2$ of the N-terminus or a side chain $NH_2$ (provided that a side chain containing $NH_2$ is present in such peptide) of either peptide to $R_2$; and (a) $R_1$ is $NH(CH_2)_n$ or $O(CH_2)_n$; and (b) $R_2$ is $(CH_2)_nNHCO$, $(CH_2)_nOCO$, $(CH_2)_nCO$, where n=1–6.

Preferred hybrid peptides of this sort include hybrid peptides which incorporate as the amylin agonist peptide: KCNTATCATQRLANELVHSSNNFGPILPPTNVGSNTY-$NH_2$ [SEQ. ID. NO. 17], wherein the cysteine residues at positions 2 and 7 are linked by a disulfide linkage, or the amylin agonist peptide, CSNLSTCVLGKLSQELHKLQTYPRTNTGSGTP-$NH_2$ [SEQ. ID. NO. 18], wherein the cysteine residues at positions 1 and 7 are linked by a disulfide linkage.

Other preferred hybrid peptides of this sort include hybrid peptides which incorporate as the CCK agonist peptide: $DY(OSO_3H)MGWMDF-NH_2$ [SEQ. ID. NO. 19], $DYMGWMDF-NH_2$ [SEQ. ID. NO. 20], $MGWMDF-NH_2$ [SEQ. ID. NO. 21], $GWMDF-NH_2$ [SEQ. ID. NO. 22], WMDF-NH [SEQ. ID. NO. 23], $KDY(OSO_3H)MGWMDF-NH_2$ [SEQ. ID. NO. 24], $KDYMGWMDF-NH_2$ [SEQ. ID. NO. 25], $KMGWMDF-NH_2$ [SEQ. ID. NO. 26], $KGWMDF-NH_2$ [SEQ. ID. NO. 27], or $KWMDF-NH_2$ [SEQ. ID. NO. 28].

In another aspect, the present invention is directed to a hybrid peptide composition comprising an amylin agonist peptide and a CCK agonist peptide covalently linked by the following structure:

wherein said amylin agonist peptide and said CCK agonist peptide are linked via the $NH_2$ of the N-terminus or side chain $NH_2$ (provided that a side chain containing $NH_2$ is present in such peptide) of either peptide to $R_1$, and via a side chain carboxylic acid of either peptide (provided that a side chain containing an carboxylic acid group is present in such peptide) to $R_5$; and (a) $R_1$ is $CONH(CH_2)n$, $COO(CH_2)n$, or $CO(CH_2)n$, where n=1–6;

(b) $R_2$ is $COONH(CH_2)_n$ (where n=1–6), $COO(CH_2)_n$ (where n=1–6), $CO(CH_2)_n$ (where n=1–6), $OCO(CH_2)_n$ (where n=1–6), $NHCO(CH_2)_n$ (where n=1–6), $OCOC_6H_4$ (ortho, meta or para linked), $COOC_6H_4$ (ortho, meta or para linked), $COOC_6H_4O$ (ortho, meta or para substituted), $NHCOC_6H_4$ (ortho, meta or para linked), $NHCOC_6H_4O$ (ortho, meta or para substituted), $CONHC_6H_4NH$ (ortho, meta or para substituted), O—X (where X is any amino acid linked via its carboxyl group, and NH—X (where X is any amino acid liked via its carboxyl group);

(c) $R_3$ is $CH_2$, $CF_2$, CO, CS or CNH;

(d) $R_4$ is O or NH; and (e) $R_5$ is $(CH_2)_n NH$ or $(CH_2)_n O$, where n=1–6;

In another aspect, the present invention is directed to a hybrid peptide composition comprising an amylin agonist peptide and a CCK agonist peptide covalently linked by the following structure:

wherein said amylin agonist peptide and said CCK agonist peptide are linked via the $NH_2$ of the N-terminus or side chain $NH_2$ (provided that a side chain containing $NH_2$ is present in such peptide) of either peptide to $R_1$, and via a side chain carboxylic acid of either peptide (provided that a side chain containing an carboxylic acid group is present in such peptide) to $R_2$; and (a) $R_1$ is $CONH(CH_2)_n$, $COO(CH_2)N$, or $CO(CH_2)N$; and (b) $R_2$ is $(CH_2)_n NH$ or $(CH_2)_n O$, where n=1–6.

Preferred such hybrid peptides of this sort include hybrid peptides which incorporate as the amylin agonist peptide: KCNTATCATQRLANFLVHSSNNFGPILPPTNVGSNTY-$NH_2$ [SEQ. ID. NO. 29], wherein the cysteine residues at positions 2 and 7 are linked by a disulfide linkage, KCNTATCATQKLANFLVHSSNNFGPILPPTNVGSNTY-$NH_2$ [SEQ. ID. NO. 30], wherein the cysteine residues at positions 2 and 7 are linked by a disulfide linkage, or CSNLSTCVLGKLSQELHKLQTYPRTNTGSGTP-$NH_2$ [SEQ. ID. NO. 31], wherein the cysteine residues at positions 1 and 7 are linked by a disulfide linkage.

Other preferred peptides of this sort include hybrid peptides which incorporate as the CCK agonist peptide: $DY(OSO_3H)MGWMDF$-$NH_2$ [SEQ. ID. NO. 32], $DYMGWMDF$-$NH_2$ [SEQ. ID. NO. 33], $MGWMDF$-$NH_2$ [SEQ. ID. NO. 34], $GWMDF$-$NH_2$ [SEQ. ID. NO. 35], $WMDF$-$NH_2$ [SEQ. ID. NO. 36], $KDY(OSO_3H)$ $MGWMDF$-$NH_2$ [SEQ. ID. NO. 37], $KDYMGWMDF$-$NH_2$ [SEQ. ID. NO. 38], $KMGWMDF$-$NH_2$ [SEQ. ID. NO. 39], $KGWMDF$-$NH_2$ [SEQ. ID. NO. 40], or $KWMDF$-$NH_2$ [SEQ. ID. NO. 41].

In another aspect, the present invention is directed to a hybrid peptide composition comprising an amylin agonist peptide and a CCK agonist peptide covalently linked by the following structure:

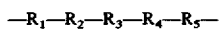

wherein said amylin agonist peptide and said CCK agonist peptide are linked via side chain carboxylic acid groups of both peptides (provided that a side chain containing an carboxylic acid group is present in such peptides); and (a) $R_1$ is $NH(CH_2)_n$ or $O(CH_2)_n$, where n=1–6;

(b) $R_2$ is $OCO(CH_2)_n$ (where n=1–6), $NHCO(CH_2)_n$ (where n=1–6), $OCOC_6H_4$ (ortho, meta or para linked), $COOC_6H_4$ (ortho, meta or para linked), $COOC_6H_4O$ (ortho, meta or para substituted), $NHCOC_6H_4$ (ortho, meta or para linked), $CONHC_6H_4$ (ortho, meta or para substituted), $CONHC_6H_4O$ (ortho, meta or para substituted), $CONHC_6H_4NH$ (ortho, meta or para substituted), O—X (where X is any amino acid linked via its carboxyl group, and NH—X (where X is any amino acid liked via its carboxyl group);

(c) $R_3$ is $CH_2$, $CF_2$, CO, CS or CNH;

(d) $R_4$ is O or NH; and (e) $R_5$ is $(CH_2)_n NHCO$ or $(CH_2)_n O$, where n=1–6;

In another aspect, the present invention is directed to a hybrid peptide composition comprising an amylin agonist peptide and a CCK agonist peptide covalently linked by the following structure:

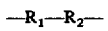

wherein said amylin agonist peptide and said CCK agonist peptide are linked via side chain carboxylic acid groups of both peptides (provided that a side chain containing an carboxylic acid group is present in such peptides); and (a) $R_1$ is $NH(CH_2)_n$ or $O(CH_2)_n$; and (b) $R_2$ is $(CH_2)_n NH$ or $(CH_2)_n O$, where n=1–6.

Preferred hybrid peptides of this sort include hybrid peptides which incorporate as the amylin agonist peptide: KCNTATCATQRLANELVHSSNNFGPILPPTNVGSNTY-$NH_2$ [SEQ. ID. NO. 42], and wherein the cysteine residues at positions 2 and 7 are linked by a disulfide linkage, or CSNLSTCVLGKLSQELHKLQTYPRTNTGSGTP-$NH_2$ [SEQ. ID. NO. 43], wherein the cysteine residues at positions 1 and 7 are linked by a disulfide linkage.

Other preferred peptides of this sort include hybrid peptides which incorporate as the CCK agonist peptide: $DY(OSO_3H)MGWMDF$-$NH_2$ [SEQ. ID. NO. 44], $DYMGWMDF$-$NH_2$ [SEQ. ID. NO. 45], $MGWMDF$-$NH_2$ [SEQ. ID. NO. 46], $GWMDF$-$NH_2$ [SEQ. ID. NO. 47], $WMDF$-$NH_2$ [SEQ. ID. NO. 48]

In one embodiment, hybrid peptides are cleavable in vivo and at least one hetero atom along the backbone of the linker of the hybrid peptide is oxygen.

In another embodiment, hybrid peptides are stable in vivo and all of the hetero atoms along the backbone of the linker of the hybrid peptide are nitrogen.

Also included within the scope of the present invention are hybrid molecules containing a linker which are produced using other methods of conjugation, such as via Michael addition of an appropriate thiol group to an appropriate mono or bis-maleimide linker. The thiol group is provided by either insertion of cysteine in the sequence of an amylin agonist or a CCK agonist or derivatisation of any lysine residues in an amylin agonist or a CCK agonist with Traut's reagent (2-iminothiolane). Examples of bis maleimides are the commercially available 1,6-bis-maleimidohexane. Other possibilities for the exploitation of lysine residues for conjugation are the use of chloroacetyl chloride, bis reductive amination with glyoxal and sodium cyanoborohydride, glucuronidation followed by periodate cleavage of the expected vicinal diol and reductive amination of the resulting aldehyde. Such methodology has been used, for example, in the chemistry of enzyme-linked immunoassays and conjugation of haptens to carrier proteins.

In another aspect, the present invention is directed to hybrid peptides which incorporate features of amylin agonist peptides and CCK agonist peptides, which hybrid peptides do not employ a linker. Thus, in one aspect, the present invention is directed to a hybrid peptide composition comprising a molecule of the following structure:

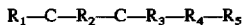

wherein:

(a) $R_1$ is either a free N-terminus or an N-terminus amidated with acetamide, proionamide, butyramide, isobutyramide, or isocaproramide; or a lysine (L) amidated with acetamide, proionamide, butyramide, isobutyramide, or isocaproramide;

(b) $R_2$ is an amino acid sequence selected from NTAT, GTAT [SEQ. ID. NO. 49], NTVT [SEQ. ID. NO. 51], NMAT [SEQ. ID. NO. 52], SNLST [SEQ. ID. NO. 53], ASLST [SEQ. ID. NO. 54] AND GNLST [SEQ. ID. NO. 55];

(c) $R_3$ is an amino acid sequence selected from ATQRLANFLVH [SEQ. ID. NO. 56] and VLGKLSQELHK [SEQ. ID. NO. 57];

(d) $R_4$ is an amino acid sequence selected from SSNNFGPILPP [SEQ. ID. NO. 58] and LQTYPR [SEQ. ID. NO. 59]; and (e) $R_5$ is an amino acid sequence selected from DYMGWMDF-$NH_2$ [SEQ. ID. NO. 60], TNTGWMDF-$NH_2$ [SEQ. ID. NO. 61], TNVGWMDF-$NH_2$ [SEQ. ID. NO. 62], TNTGWLDF-$NH_2$ [SEQ. ID. NO. 63], TNVGWLDF-$NH_2$ [SEQ. ID. NO. 64], TNTGSNDF-$NH_2$ [SEQ. ID. NO. 65], TNVGSNDF-$NH_2$ [SEQ. ID. NO. 66], TNTGSNDY-$NH_2$ [SEQ. ID. NO. 67] and TNVGSNDY-$NH_2$ [SEQ. ID. NO. 68].

Preferred non-linker type hybrid peptides of this sort include the following:
KCNTATCATQRLANFLVHSSNNFGPILPPDYMG-WMDF-$NH_2$ [SEQ. ID. NO. 69];
CSNLSTCVLGKLSQELHKLQTYPRDYMGWMDF-$NH_2$ [SEQ. ID. NO. 70];
KCNTATCATQRLANFLVHSSNNFGPILPPTNTGWM-DF-$NH_2$ [SEQ. ID. NO. 71];
CSNLSTCVLGKLSQELHKLQTYPRTNTGWMDF-$NH_2$ [SEQ. ID. NO. 72];
KCNTATCATQRLANFLVHSSNNFGPILPPTNTGWL-DF-$NH_2$ [SEQ. ID. NO. 73];
CSNLSTCVLGKLSQELHKLQTYPRTNTGWLDF-$NH_2$ [SEQ. ID. NO. 74];
KCNTATCATQRLANFLVHSSNNFGPILPPTNVGSN-DF-$NH_2$ [SEQ. ID. NO. 75];
CSNLSTCVLGKLSQELHKLQTYPRTNVGSNDF-$NH_2$ [SEQ. ID. NO. 76];
KCNTATCATQRLANFLVHSSNNFGPILPPTNVGSN-DY-$NH_2$ [SEQ. ID. NO. 77]; and
CSNLSTCVLGKLSQELHKLQTYPRTNVGSNDY-$NH_2$ [SEQ. ID. NO. 78].

Also within the scope of the invention are compounds in which amylin agonists, CCK agonists and hybrid peptides are modified by substituting certain amino acids for others having similar properties which will result in retention of biological activity. Typical substitutions are leucine for methionine or vice versa, valine for isoleucine or vice versa, glutamine for asparagine or vice versa, phenylalamine for tyrosine or vice versa, arginine for lysine or vice versa, aspartic acid for glutamic acid or vice versa, the interchange of threonine, serine and alanine, the interchange of histidine, tryptophan, the interchange of histidine, tryptophan, phenylalamine acid and tyrosine. In addition, other substitutions involving unnatural amino acids are included within the scope of the invention, such as t-leucine or penicillamine and derivative for valine or isoleucine, p-substituted phenylalamine for phenylalanine or tyrosine amino isobutyric acid for alanine, serine, threonine or valine.

Biologically active derivatives of the above-described compounds are also included within the scope of this invention in which the stereochemistry of individual amino acids may be inverted from (L)/S to (D)/R at one or more specific sites.

Also included within the scope of this invention are the compounds in which amylin agonists or CCK agonists are modified by glycosylation of Ash, Ser and/or Thr residues.

Also included within the scope of the present invention are biologically active compounds as described above which contain less peptide character. Such peptide mimetics may include, for example, one or more of the following substitutions for —CO—NH— amide bonds: depsipeptides (—CO—O—), iminomethylenes (—$CH_2$—NH—), trans-alkenes (—CH=CH—), β-enaminonitriles (—C(=CH—CN)—NH—), thioamides (—CS—NH—), thiomethylenes (—S—$CH_2$— or —$CH_2$—S—), methylenes (—$CH_2$—$CH_2$—) and retro-amides (—NH—CO—).

The hybrid compositions of the present invention are useful, for example, in the claimed methods for reducing food intake, controlling appetite and control of body weight.

The dosages of hybrid peptide compositions will vary depending on the composition, and are preferably in amounts of between about 0.1 µg/kg/day to about 1 µg/kg/day, preferably 0.1 µg/kg/day to about 10 µg/kg/day, and more preferably 0.1 µg/kg/day to about 1 µg/kg/day.

BRIEF DESCRIPTION OF THE DRAWINGS

The invention will be further described with reference to the accompanying drawing in which.

DETAILED DESCRIPTION OF THE INVENTION

Amylin Agonists

Figure 1:
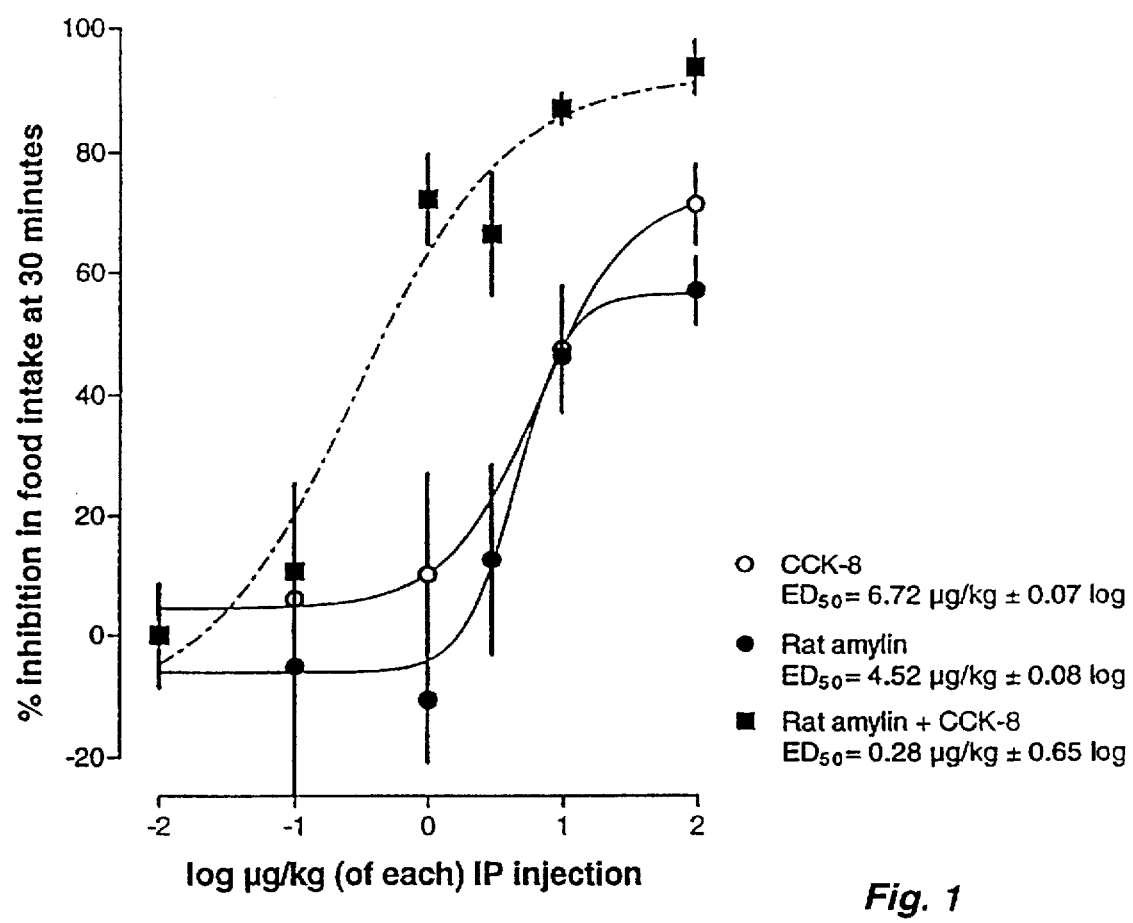
FIG. 1 shows the dose response for appetite suppression in mice of rat amylin (open triangles), CCK-8 (open circles) and rat amylin plus CCK-8 (open squares). Rat amylin (1.0 µg/kg) and CCK-8 (1.0 µg/kg) alone and in combination suppressed food intake in mice at 30 minutes. Rat amylin plus CCK-8 suppressed food intake by 72.3±7.5% (P<0.0006). Rat amylin alone suppressed food intake by −10.5±10.3%. CCK-8 alone suppressed food intake by 10.6±16.9%.

The nomenclature of various amylin agonists can be used to indicate both the peptide that the sequence is based on and the modifications made to any basic peptide amylin sequence, such as human amylin. An amino acid preceded by a superscript number indicates that the named amino acid replaces the amino acid normally present at the amino acid position of the superscript in the basic amino acid sequence. For example, "[18]Arg[25,28]Pro-h-amylin" refers to a peptide based on the sequence of "h-amylin" or "human-amylin" having the following substitutions: Arg replacing His at residue 18, Pro replacing Ala at residue 25 and Pro replacing Ser at residue 28. The term "des-[1]Lys-h-amylin" refers to a peptide based on the sequence of human amylin, with the first, or N-terminal, amino acid deleted.

Activity as amylin agonist agents can be indicated by activity in the receptor binding assay and the soleus muscle assay described below. Amylin agonist activity of compounds may also be assessed by the ability to induce hyperlactemia and/or hyperglycemia in mammals, to reduce post-prandial plasma glucose levels, to slow gastric emptying, or to reduce food intake, as described herein. Preferred amylin agonists are described herein.

Preferred amylin agonist compounds des-$^1$Lys-h-amylin [SEQ. ID. NO. 79], $^{28}$Pro-h-amylin [SEQ. ID. NO. 80], $^{25,28,29}$Pro-h-amylin [SEQ. ID. NO. 81], $^{18}$Arg$^{25,28}$Pro-h-amylin [SEQ. ID. NO. 82], and des-$^1$Lys$^{18}$Arg$^{25,28}$Pro-h-amylin [SEQ. ID. NO. 83], all show amylin activity in vivo in treated test animals, provoking marked hyperlactemia followed by hyperglycemia. In addition to having activities characteristic of amylin, certain preferred compounds have also been found to possess more desirable solubility and stability characteristics when compared to human amylin. These preferred compounds include $^{25}$Pro$^{26}$Val$^{28,29}$Pro-h-amylin [SEQ. ID. NO. 84], $^{25,28,29}$Pro-h-amylin [SEQ. ID. NO. 81] (also referred to herein as "AC-0137"), and $^{18}$Arg$^{25,28}$Pro-h-amylin [SEQ. ID. NO. 82].

The methods and compositions of the present invention employ an amylin agonist, including an amylin or an amylin agonist analogue, for example, amylin receptor agonist analogues such as $^{18}$Arg$^{25,28}$Pro-h-amylin [SEQ. ID. NO. 82], des-$^1$Lys$^{18}$Arg$^{25,28}$Pro-h-amylin [SEQ. ID. NO. 83], $^{18}$Arg$^{25-28,29}$Pro-h-amylin [SEQ. ID. NO. 85], des-$^1$Lys$^{18}$Arg$^{25,28,29}$Pro-h-amylin [SEQ. ID. NO. 86], $^{25,28}$Pro-h-amylin [SEQ. ID. NO. 87], des-$^1$Lys$^{25,28,29}$Pro-h-amylin [SEQ. ID. NO. 88], and $^{25}$Pro$^{26}$Val$^{25,28}$Pro-h-amylin [SEQ. ID. NO. 89]. Examples of other suitable amylin agonist analogues include:

$^{23}$Leu$^{25}$Pro$^{26}$Val$^{28,29}$Pro-h-amylin [SEQ. ID. NO. 90];

$^{23}$Leu$^{25}$Pro$^{26}$Val$^{28}$Pro-h-amylin [SEQ. ID. NO. 91];

des-$^1$Lys$^{23}$Leu$^{25}$Pro$^{26}$Val$^{28}$Pro-h-amylin [SEQ. ID. NO. 92];

$^{18}$Arg$^{23}$Leu$^{25}$Pro$^{26}$Val$^{28}$Pro-h-amylin [SEQ. ID. NO. 93];

$^{18}$Arg$^{23}$Leu$^{25,28,29}$Pro-h-amylin [SEQ. ID. NO. 94];

$^{18}$Arg$^{23}$Leu$^{25,28}$Pro-h-amylin [SEQ. ID. NO. 95];

$^{17}$Ile$^{23}$Leu$^{25,28,29}$Pro-h-amylin [SEQ. ID. NO. 96];

$^{17}$Ile$^{25,28,29}$Pro-h-amylin [SEQ. ID. NO. 97];

des-$^1$Lys$^{17}$Ile$^{23}$Leu$^{25,28,29}$Pro-h-amylin [SEQ. ID. NO. 98];

$^{17}$Ile$^{18}$Arg$^{23}$Leu-h-amylin [SEQ. ID. NO. 99];

$^{17}$Ile$^{18}$Arg$^{23}$Leu$^{26}$Val$^{29}$Pro-h-amylin [SEQ. ID. NO. 100];

$^{17}$Ile$^{18}$Arg$^{23}$Leu$^{25}$Pro$^{26}$Val$^{28,29}$Pro-h-amylin [SEQ. ID. NO. 101];

$^{13}$Thr$^{21}$His$^{23}$Leu$^{26}$Ala$^{28}$Leu$^{29}$Pro$^{31}$Asp-h-amylin [SEQ. ID. NO. 102];

$^{13}$Thr$^{21}$His$^{23}$Leu$^{26}$Ala$^{29}$Pro$^{31}$Asp-h-amylin [SEQ. ID. NO. 103];

des-$^1$Lys$^{13}$Thr$^{21}$His$^{23}$Leu$^{26}$Ala$^{28}$Pro$^{31}$Asp-h-amylin [SEQ. ID. NO. 104];

$^{13}$Thr$^{18}$Arg$^{21}$His$^{23}$Leu$^{26}$Ala$^{29}$Pro$^{31}$Asp-h-amylin [SEQ. ID. NO. 105];

$^{13}$Thr$^{18}$Arg$^{21}$His$^{23}$Leu$^{28,29}$Pro$^{31}$Asp-h-amylin [SEQ. ID. NO. 106]; and, $^{13}$Thr$^{18}$Arg$^{21}$His$^{23}$Leu$^{25}$Pro$^{26}$Ala$^{28,29}$Pro$^{31}$Asp-h-amylin [SEQ. ID. NO. 107].

Still further amylin agonists including amylin agonist analogues are disclosed in commonly owned U.S. patent application, entitled, "Novel Amylin Agonist Peptides and Uses Therefor," filed May 30, 1995 (docket no. 213/080), and corresponding PCT application, Publication No. WO 93/10146, published May 27, 1993, the disclosures of which is hereby incorporated by this reference.

Other amylin agonists included calcitonins and modifications thereof. The term "calcitonin" is used in a manner well known by those in the art (see, Azria, Calcitonins—Physiological and Pharmacological Aspects, pp. 1–31, Springer-Verlag, 1989). For example, the term is meant to include peptides similar to a 32 amino acid peptide isolated from porcine thyroid glands. The hormone is synthesized and secreted by the parafollicular C cells of the thyroid gland in mammals. Calcitonins from several submammalian vertebrates have been sequenced. In these submammalian species, calcitonin is stored in cells located in the ultimobranchial body, which is separated from the thyroid gland. Calcitonins from fish (e.g., salmon and eel), and the closely related chicken calcitonin, are sometimes termed ultimobranchial calcitonins due to their location in ultimobranchial bodies.

The term is also meant to include peptides or their equivalent having similar amino acid sequences to known calcitonins and having one or more of the known biological activities, but at least the ability to reduce food intake in mammals. Such peptides include those referred to as functional equivalents or functional calcitonin fragments, and conservative variants thereof.

As set forth in U.S. Pat. No. 5,321,008, the ultimobranchial calcitonins were found to have very high affinity in the receptor assay discussed below, which affinity is similar to that of amylin itself. Rat and human calcitonin have very low affinities for amylin receptors. The other calcitonins are useful as amylin agonists in this invention.

TABLE 1

| Peptide | Receptor Binding (IC$_{50}$, nM) | Soleus Muscle (EC$_{50}$, nM) |
| --- | --- | --- |
| Human amylin | 0.05 | 1.6 |
| Chicken calcitonin | 0.03 | 0.7 |
| Salmon calcitonin | 0.07 | 0.4 |
| Eel calcitonin | 0.09 | 0.4 |
| 1.7-Asn-eel Calcitonin | 0.05 | 0.3 |

CCK Agonists

CCK and various agonists of CCK are known in the art. CCK agonists include CCKs as well as species variants of the amino acid sequence of CCK, for example, the 33-amino acid sequence first identified in humans and its 8-amino acid C-terminal have been reportedly demonstrated in pig, rat, chicken, chinchilla, dog and humans. Other species variants include a 39-amino acid sequence found in pig, dog and guinea pig, and a 58-amino acid found in cat, dog and humans, and a 47-amino acid sequences homologous to both CCK and gastrin. Gastrin is also a CCK agonist. The C-terminal sulfated octapeptide sequence, Asp-Tyr(SO$_3$H)-Met-Gly-Trp-Met-Asp-Phe-NH$_2$ [SEQ. ID. NO. 108], is relatively conserved across species, and may be the minimum sequence for biological activity in the periphery of rodents. Thus, CCK agonists include human CCK-33 itself, sulfated CCK-8 (CCK26–33), unsulfated CCK-8, pentagastrin (CCK-5 or CCK(29–33)), and the tetrapeptide, CCK-4 (CCK30–33).

The type A receptor subtype (CCK$_A$) has been reported to be selective for the sulfated octapeptide. The Type B receptor subtype (CCK$_B$) has been identified throughout the brain and in the stomach, and reportedly does not require sulfation or all eight amino acids. $CCK_A$ agonists also include A-71623 and A-708874, which were developed based on the structure of CCK-4. Members of another series of $CCK_A$ agonists, which includes JMV-180, are reportedly active in stimulating pancreatic amylase release and inhibiting feeding. Examples of non-peptide $CCK_A$ agonists are L-364718 and FPL 15849KF (Hpa($SO_3$H)-Nle-Gly-Trp-Nle-MeAsp-Phe-$NH_2$) [SEQ. ID. NO. 109]. $CCK_B$ agonists include CCK-8, unsulfated CCK-8, CCK-4, and BC 264 (which is a peptidase-resistant CCK derivative).

Various in vivo and in vitro screening methods for CCK agonists are known in the art. Examples include in vivo assays involving the contraction of the dog or guinea pig gallbladder after rapid intravenous injection of the compound to be tested for CCK-like activity, and in vitro assays measuring using strips of rabbit gallbladder. See Walsh, "Gastrointestinal Hormones," In Physiology of the Gastrointestinal Tract (3d ed. 1994; Raven Press, New York).

Assays

The activity of amylin agonists may be evaluated using certain biological assays described herein. The receptor binding assay can identify both candidate amylin agonists and antagonists and can be used to evaluate binding, while the soleus muscle assay distinguishes between amylin agonists and antagonists.

Preferably, amylin agonist compounds exhibit $EC_{50}$s in the amylin receptor binding assay as described above, but more preferably, as noted, on the order of less than about 1 to 5 nM, preferably less than about 1 nM and more preferably less than about 50 pM. In the soleus muscle assay these compounds preferably show $EC_{50}$ values on the order of less than about 1 to 10 micromolar.

The amylin receptor binding assay is described in U.S. Pat. No. 5,264,372, issued Nov. 23, 1993, the disclosure of which is incorporated herein by reference. The receptor binding assay is a competition assay which measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et. al. (ALLFIT, Version 2.7 (NIH, Bethesda, Md. 20892)). Munson, P. and Rodbard, D., Anal. Biochem. 107:220–239 (1980).

Assays of biological activity of amylin agonists, including amylin agonist analogue preparations, in the soleus muscle are performed using previously described methods (Young et al., Am. J. Physiol. 263:E274–281 (1992). In summary, amylin agonist activity is assessed by measuring the inhibition of insulin-stimulated glycogen synthesis in soleus muscle. Amylin antagonist activity is assessed by measuring the resumption of insulin-stimulated glycogen synthesis in the presence of 100 nM rat amylin and an amylin antagonist. Concentrations of peptide dissolved in carrier-free buffers are determined by quantitative amino acid analysis, as described therein. The ability of compounds to act as agonists in this assay is determined by measuring $EC_{50}$ values. Standard errors are determined by fitting of sigmoidal dose response curves using a four parameter logistic equation (De Lean, A., Munson, P. J., Guardabasso, V. and Rodbard, D. (1988) ALLFIT, Version 2.7, National Institute of Child Health and Human Development, N.I.H. Bethesda, Md., 1 diskette). A number of amylin agonists have been characterized using these biological assays. For example, the compounds $^{18}$Arg$^{25,28}$Pro-h-amylin, des$^1$Lys$^{18}$Arg$^{25,28}$Pro-h-amylin, $^{18}$Arg$^{25,28,29}$Pro-h-amylin, des-$^1$Lys$^{18}$Arg$^{25,28,29}$Pro-h-amylin, $^{25,28,29}$Pro-h-amylin, des-$^1$Lys$^{25,28,29}$Pro-h-amylin, and $^{25}$Pro$^{26}$Val$^{25,28}$Pro-h-amylin were all found to compete with amylin in the receptor binding assay. These compounds have negligible antagonist activity as measured by the soleus muscle assay and were shown to act as amylin agonists.

Preparation of Compounds

Preferably, peptide amylin agonists, peptide CCK agonists and hybrid peptides are synthezised using standard solid phase synthesis methodology based on Fmoc chemistry and the Rink resin (i.e., 4-methylbenzhydryl-amine resin) which allows the direct generation of a C-terminal amide at the end of the synthesis. All cholecystokinin-like peptides are synthezised either by standard solid phase synthesis methods using Fmoc chemistry and the Rink resin which allows the direct generation of a C-terminal amide at the end of the synthesis or by standard solution chemistry.

Preferably, such methods are carried out using an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin to be used in a peptide synthesizer are purchased from Applied Biosystems Inc. (Foster City, Calif.). Side-chain protected amino acids are purchased from Applied Biosystems, Inc., and include the following: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr (BrZ), Fmoc-Tyr(t-Bu), Boc-Lys(Cl-Z), Fmoc-Lys(Boc), Boc-Glu(Bzl), Fmoc-Glu(t-Bu), Fmoc-His(Trt), Fmoc-Asn (Trt), and Fmoc-Gln(Trt). Boc-His(BOM) are purchased from Applied Biosystems, Inc. or Bachem Inc. (Torrance, Calif.). Anisole, methylsulfide, phenol, ethanedithiol, and thioanisole are obtained from Aldrich Chemical Company (Milwaukee, Wis.). Air Products and Chemicals (Allentown, Pa.) supplies HF. Ethyl ether, acetic acid and methanol are purchased from Fisher Scientific (Pittsburgh, Pa.).

Solid phase peptide synthesis is carried out with an automatic peptide synthesizer (Model 430A, Applied Biosystems Inc., Foster City, Calif.) using the NMP/HOBt (Option 1) system and Tboc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping. Boc-peptide-resins are cleaved with HF (−5° C. to 0° C., 1 hour). The peptide is extracted from the resin with alternating water and acetic acid, and the filtrates are lyophilized. The Fmoc-peptide resins are cleaved according to standard methods (*Introduction to Cleavage Techniques,* Applied Biosystems, Inc., 1990, pp. 6–12). Peptides are also assembled using an Advanced Chem Tech Synthesizer (Model MPS 350, Louisville, Ky.). Such peptides are purified by RP-HPLC (preparative and analytical) using a Waters Delta Prep 3000 system. A C4, C8 or C18 preparative column (10μ, 2.2×25 cm; Vydac, Hesperia, Calif.) are used to isolate peptides, and purity was determined using a C4, C8 or C18 analytical column (5μ, 0.46×25 cm; Vydac). Solvents (A=0.1% TFA/water and B=0.1% TFA/$CH_3CN$) are delivered to the analytical column at a flowrate of 1.0 ml/min and to the preparative column at 15 ml/min. Amino acid analyses are performed on the Waters Pico Tag system and processed using the Maxima program. The peptides are hydrolyzed by vapor-phase acid hydrolysis (115° C., 20–24 h). Hydrolysates is derivatized and analyzed by standard methods (Cohen, S. A., Meys, M., and Tarrin, T. L. (1989), *The Pico Tag Method: A Manual of Advanced Techniques for Amino Acid Analysis,* pp. 11–52, Millipore Corporation, Milford, Mass.). Fast atom bombardment analysis is carried out by M-Scan, Incorporated (West Chester, Pa.). Mass calibration is performed using cesium iodide or cesium iodide/glycerol. Plasma desorption ionization analysis using time of flight detection can be carried out on an Applied Biosystems Bio-Ion 20 mass spectrometer.

Peptide compounds useful in the invention may also be prepared using recombinant DNA techniques, using methods now known in the art. See, e.g., Sambrook et al., *Molecular Cloning: A Laboratory Manual,* 2d Ed., Cold Spring Harbor (1989).

In preparation of hybrid peptides linked by a linker, typically, N-terminal linkage of the two peptides is achieved as follows: the amylin agonist is left on the resin in its fully protected form. However, disulphide bridge formation is carried out on the resin. The N-terminal Fmoc group is removed and allowed to react with the appropriately activated bi-functional linker which in turn is either commercially available or is prepared by standard methods of organic synthesis. For example, methods for preparation of bi-functional linkers are described in Weber et al., *Bioconj. Chem.* 1:431–437 (1990); Arano et al., *Bioconj. Chem.* 2:71–76 (1991); Quadri et al., In "Cancer Imaging with Radiolabelled Antibodies" (Goldenberg, ed. 1990) pages 201–213; King et al., *Cancer Research* 54:6176–6185 (1994). Typical activation is the formation of an N-hydroxy succinimide ester with N-hydroxy succinimide and dicyclohexylcarbodiimide. The other end of the bi-functional linker is deprotected, if necessary, and activated as above then allowed to react with a fully protected, N-terminal free, CCK agonist analogue. Side chain deprotection and removal from the resin is achieved under standard conditions. All cross-linked bis-peptides are purified by reverse phase $C^{18}$ HPLC eluting typically with an acetonitrile/aqueous TFA gradient followed by lyophilization. All cross-linked bis-peptides are characterized by electrospray mass spectrometry and purity determined by reverse phase $C^{18}$ HPLC. Linkage via side chains and other permutations are achieved largely by the above procedure except the basic side chains are protected in such a way that they may be selectively revealed and carboxylate side chains are protected in such a way that they may be selectively revealed and activated. Protecting groups for both of these options are well known in the art. An example of a protecting group for a basic side chain is the chemically stable, but photochemically labile, NVOC group. An example of a protecting group for an acidic side chain is the trichloroethyl ester which can then be selectively cleaved with zinc/acetic acid.

The compounds referenced above form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Formulations

Compositions useful in the invention may conveniently be provided in the form of formulations suitable for parenteral (including intramuscular and subcutaneous) or nasal or transdermal, or suitably encapsulated or otherwise prepared art-known methods for oral administration. In some cases, it will be convenient to provide an amylin agonist and CCK agonist in a single composition or solution for administration together. In other cases, it may be more advantageous to administer a CCK agonist separately from an amylin agonist. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology,* Technical Report No. 10, Supp. 42:2S (1988).

Compounds useful in the invention can be provided as parenteral compositions for injection or infusion. Preferably, they are dissolved in an aqueous carrier, for example, in an isotonic buffer solution at a pH of about 4.3 to 7.4. These compositions may be sterilized by conventional sterilization techniques, or may be sterile filtered. The compositions may contain pharmaceutically acceptable auxiliary substances as required to stabilize the formulation, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions may be thickened with a thickening agent such as methyl cellulose.

Compositions useful in the invention are prepared by mixing the ingredients following generally accepted procedures. For example, the selected components may be mixed in a blender or other standard device to produce a concentrated mixture which may then be adjusted to the final concentration and viscosity by the addition of water or thickening agent and possibly a buffer to control pH or an additional solute to control tonicity.

Dosages

For use by the physician, the compositions will be provided in dosage unit form containing an amount of a compound of the invention (with or without another feeding suppressing agent) which will be effective in one or multiple doses to control appetite at the selected level. Therapeutically effective amounts of an amylin agonist and a CCK agonist, or a hybrid peptide, for use in the suppressing of food intake and in conditions in which food intake is beneficially reduced are those that reduce food intake as desired. Such dosages of each of an amylin agonist and a CCK agonist are between about 0.1 µg/kg/day and about 10 µg/kg/day, preferably between about 0.1 µg/kg/day and about 1 µg/kg/day, per agonist, administered in a single dose or in multiple doses. Such dosages of hybrid peptides are between about 0.1 µg/kg/day and about 1 mg/kg/day, preferably between about 0.1 µg/kg/day and about 10 µg/kg/day, and more preferably between about 0.1 µg/kg/day and 1 µg/kg/day. Generally, in suppressing appetite, the compounds of this invention may be administered to patients in need of such treatment in a dosage ranges similar to those given above, however, the compounds are administered more frequently, for example, one, two, or three times a day. As will be recognized by those in the field, an effective amount of therapeutic agent will vary with many factors including the age and weight of the patient, the patient's physical condition and other factors. Orally active compounds may be taken orally, however, dosages should be increased 5–10 fold, or should be increased (or decreased) in the ratio described earlier. As noted above, an advantage of the synergy between an amylin agonist and a CCK agonist discovered by applicants is that it allows dosages sufficiently low that methods of administering peptides, modified peptides or encapsulated peptide preparations having low (i.e., about 10–20%) bioavailability to be administered, for example, nasally, transdermally or orally, in such amounts to achieve systemic levels sufficient to produce control of food intake.

The following Example is illustrative, but not limiting of the methods and compositions of the present invention. Other suitable compounds that may be modified or adapted for use are also appropriate and are within the spirit and scope of the invention.

EXAMPLE 1

Male NIH/Swiss Webster (Hsd:NIHS) mice, 8–10 weeks of age, were obtained from Harlan Sprague Dawley, Madison, Wis. Animals were exposed to 12:12 hour light-dark cycle, with lights off at 18:00, and with room temperature between 22° and 25° C. Water and food (Teklan 7002, Harlan Teklad, Madison, Wis.) were available ad libitum except as indicated below. Animals were adapted to the vivarium environment for at least one week before experiments were carried out.

Rat amylin (AC128) was synthesized by Fmoc solid phase synthesis. Cholecystokinin octapeptide 26–33 (CCK-8) was obtained from Peninsula Laboratories (Belmont, Calif.). Peptides were dissolved in sterile water to obtain stock solutions of 1 mg/ml. Further dilutions were made with sterile saline just prior to intraperitoneal injections.

Animals were individually housed and deprived of food for 18–20 hours before experiments. Animals were allowed ad libitum access to water before and during the experiments. Immediately after intraperitoneal injection of rat amylin or CCK-8 or saline, all animals received a pre-weighed pellet of food. Food intake for each animal was measured by weighing the food pellet at 30 minutes following injection and providing food.

As shown in FIG. 1, rat amylin (AC128) (1.0 µg/kg) and CCK-8 (1.0 µg/kg) alone and in combination suppressed food intake in mice at 30 minutes. Rat amylin plus CCK-8 suppressed food intake by 72.3±7.5% (P<0.0006). Rat amylin alone suppressed food intake by −10.5±10.3% (not significant). CCK-8 alone suppressed food intake by 10.6±16.9% (not significant). The dose response for appetite suppression in mice of rat amylin (AC128) (filled circles), CCK8 (open circles) and rat amylin plus CCK (filled squares) is also shown in FIG. 1.

Thus, rat amylin plus CCK-8 had a synergistic effect and dose-dependently suppressed food intake in mice after 30 minutes, by up to 93% (at 100 µg), with an $ED_{50}$ of 0.28 µg/kg±0.65 log units. These experiments indicate that the combination of an amylin agonist and a CCK agonist at doses that are about 100- to 3-fold lower than the $ED_{50}$ for the respective peptides in mice, and at doses that are about equal to or 10-fold lower than the minimally effective doses of such peptides given individually, can provide effective regulation of food intake.

---

What is claimed is:

1. A composition comprising an amylin agonist and a CCK agonist admixed in a pharmaceutically acceptable carrier.

2. A composition according to claim 1 wherein said amylin agonist is $^{25,28,29}$Pro-h-amylin [SEQ. ID. NO. 81].

3. A composition according to claim 1 wherein said amylin agonist is s-calcitonin.

4. A composition according to claim 1 wherein said amylin agonist is h-amylin.

5. A composition according to claim 1 wherein said CCK agonist is a $CCK_A$ agonist.

6. A composition according to claim 1 wherein said CCK agonist is CCK-8.

7. A method for reducing food intake in a mammal comprising administering to said mammal an effective food intake-reducing combination of an amylin agonist and a CCK agonist.

8. A method for the control of appetite in a mammal comprising co-administering to said mammal therapeutically effective amounts of an amylin agonist and a CCK agonist.

9. A method for the control of body weight of a subject comprising co-administering to said subject an effective food intake-reducing combination of an amylin agonist and a CCK agonist.

10. A method according to claim any of claims 7, 8 or 9 wherein said amylin agonist is h-amylin.

11. A method according to any of claims 7, 8 or 9 wherein said amylin agonist is s-calcitonin.

12. A method according to any of claims 7, 8 or 9 wherein said amylin agonist is $^{25,28,29}$Pro-h-amylin [SEQ. ID. NO. 81].

13. A method according to any of claims 7, 8 or 9 wherein said CCK agonist is a $CCK_A$ agonist.

14. A method according to any of claims 7, 8 or 9 wherein said $CCK_A$ agonist is CCK-8.

15. A method according to any of claims 7, 8 or 9 wherein said amylin agonist and said CCK agonist are each administered in an amount of between about 0.1 µg/kg/day to about 10 µg/kg/day.

16. A method according to any of claims 7, 8 or 9 wherein said amylin agonist and said CCK agonist are each administered in an amount of between about 0.1 µg/kg/day to about 1 µg/kg/day.

17. A hybrid peptide composition comprising an amylin agonist peptide and a CCK agonist peptide covalently linked by the following structure:

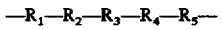

wherein said amylin agonist peptide and said CCK agonist peptide are linked via the $NH_2$ of the N-terminus of either peptide and/or via a side chain $NH_2$ of either peptide (provided that a side chain containing an $NH_2$ is present in such peptide); and (a) $R_1$ is $CONH(CH_2)N$, $COO(CH_2)n$, or $CO(CH_2)n$, where n=1–6;

(b) $R_2$ is $OCO(CH_2)_n$ (where n=1–6), $NHCO(CH_2)_n$ (where n=1–6), $OCOC_6H_4$ (ortho, meta or para linked), $COOC_6H_4$ (ortho, meta or para linked), $COOC_6H_4O$ (ortho, meta or para substituted), $NHCOC_6H_4$ (ortho, meta or para linked), $NHCOC_6H_4O$ (ortho, meta or para substituted), $CONHC_6H_4NH$ (ortho, meta or para substituted), O—X (where X is any amino acid linked via its carboxyl group, and NH—X (where X is any amino acid liked via its carboxyl group);

(c) $R_3$ is $CH_2$, $CF_2$, CO, CS or CNH;

(d) $R_4$ is O or NH; and (e) $R_5$ is $(CH_2)_nNHCO$, $(CH_2)_nOCO$, $(CH_2)_nCO$, where n=1–6.

18. A hybrid peptide composition comprising an amylin agonist peptide and a CCK agonist peptide covalently linked by the following structure:

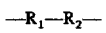

wherein said amylin agonist peptide and said CCK agonist peptide are linked via the $NH_2$ of the N-terminus of either peptide and a side chain $NH_2$ of either peptide (provided that a side chain containing an $NH_2$ is present in such peptide); and (a) $R_1$ is $CONH(CH_2)_n$, $COO(CH_2)N$, or $CO(CH_2)N$; and (b) R2 is $(CH_2)_nNHCO$, $(CH_2)_nOCO$, $(CH_2)_nCO$, where n=1–6.

19. A hybrid peptide according to claim 17 or claim 18 wherein said amylin agonist peptide has the following sequence:
KCNTATCATQRLANFLVHSSNNFGPILPPTNVGSNT-Y-$NH_2$ [SEQ. ID. NO. 4] and wherein the cysteine residues at positions 2 and 7 are linked by a disulfide linkage.

20. A hybrid peptide according to claim 17 or claim 18 wherein said amylin agonist peptide has the following sequence:
KCNTATCATQKLANFLVHSSNNFGPILPPTNVGSNT-Y-$NH_2$ [SEQ. ID. NO. 5] and wherein the cysteine residues at positions 2 and 7 are linked by a disulfide linkage.

21. A hybrid peptide according to claim 17 or claim 18 wherein said amylin agonist peptide has the following sequence:
CSNLSTCVLGKLSQELHKLQTYPRTNTGSGTP-$NH_2$ [SEQ. ID. NO. 6] wherein the cysteine residues at positions 1 and 7 are linked by a disulfide linkage.

22. A hybrid peptide according to claim 17 or claim 18 wherein said CCK agonist peptide has the following sequence:
DY($OSO_3H$)MGWMDF-$NH_2$ [SEQ. ID. NO. 7].

23. A hybrid peptide according to claim 17 or claim 18 wherein said CCK agonist peptide has the following sequence:
DYMGWMDF-$NH_2$ [SEQ. ID. NO. 8].

24. A hybrid peptide according to claim 17 or claim 18 wherein said CCK agonist peptide has the following sequence:
MGWMDF-$NH_2$ [SEQ. ID. NO. 9].

25. A hybrid peptide according to claim 17 or claim 18 wherein said CCK agonist peptide has the following sequence:
GWMDF-$NH_2$ [SEQ. ID. NO. 10].

26. A hybrid peptide according to claim 17 or claim 18 wherein said CCK agonist peptide has the following sequence:
WMDF-$NH_2$ [SEQ. ID. NO. 11].

27. A hybrid peptide according to claim 17 or claim 18 wherein said CCK agonist peptide has the following sequence:
KDY($OSO_3H$)MGWMDF-$NH_2$ [SEQ. ID. NO. 12].

28. A hybrid peptide according to claim 17 or claim 18 wherein said CCK agonist peptide has the following sequence:
KDYMGWMDF-$NH_2$ [SEQ. ID. NO. 13].

29. A hybrid peptide according to claim 17 or claim 18 wherein said CCK agonist peptide has the following sequence:
KMGWMDF-$NH_2$ [SEQ. ID. NO. 14].

30. A hybrid peptide according to claim 17 or claim 18 wherein said CCK agonist peptide has the following sequence:
KGWMDF-$NH_2$ [SEQ. ID. NO. 15].

31. A hybrid peptide according to claim 17 or claim 18 wherein said CCK agonist peptide has the following sequence:
KWMDF-$NH_2$ [SEQ. ID. NO. 16].

32. A hybrid peptide composition comprising an amylin agonist peptide and a CCK agonist peptide covalently linked by the following structure:

wherein said amylin agonist peptide and said CCK agonist peptide are linked via the side chain carboxylic acid group of either peptide (provided that a side chain containing an carboxylic acid group is present in such peptide) to $R_1$, and via the $NH_2$ of the N-terminus or a side chain $NH_2$ of either peptide (provided that a side chain containing $NH_2$ is present in such peptide) to $R_5$; and (a) $R_1$ is $NH(CH_2)_n$ or $O(CH_2)_n$, where n=1–6;

(b) $R_2$ is $OCO(CH_2)_n$ (where n=1–6), $NHCO(CH_2)_n$ (where n=1–6), $OCOC_6H4_b$ (ortho, meta or para linked), $COOC_6H_4$ (ortho, meta or para linked), $COOC_6H_4O$ (ortho, meta or para substituted), $NHCOC_6H4_b$ (ortho, meta or para linked), $NHCOC_6H_4O$ (ortho, meta or para substituted), $CONHC_6H_4NH$ (ortho, meta or para substituted), O—X (where X is any amino acid linked via its carboxyl group, and NH—X (where X is any amino acid liked via its carboxyl group);

(c) $R_3$ is $CH_2$, $CF_2$, CO, CS or CNH;
(d) $R_4$ is O or NH; and
(e) $R_5$ is $(CH_2)_n NHCO$, $(CH_2)_n OCO$, $(CH_2)_n CO$, where n=1–6.

33. A hybrid peptide composition comprising an amylin agonist peptide and a CCK agonist peptide covalently linked by the following structure:

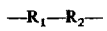

wherein said amylin agonist peptide and said CCK agonist peptide are linked via the side chain carboxylic acid group of either peptide (provided that a side chain containing an carboxylic acid group is present in such peptide) to $R_1$, and via the $NH_2$ of the N-terminus or a side chain $NH_2$ (provided that a side chain containing $NH_2$ is present in such peptide) of either peptide to $R_2$; and (a) $R_1$ is $NH(CH_2)_n$ or $O(CH_2)_n$; and
(b) $R_2$ is $(CH_2)_n NHCO$, $(CH_2)_n OCO$, $(CH_2)_n CO$, where n=1–6.

34. A hybrid peptide according to claim 32 or claim 33 wherein said amylin agonist peptide has the following sequence:
KCNTATCATQRLANELVHSSNNFGPILPPTNVGSNT-Y-NH$_2$ [SEQ. ID. NO. 17] and wherein the cysteine residues at positions 2 and 7 are linked by a disulfide linkage.

35. A hybrid peptide according to claim 32 or claim 33 wherein said amylin agonist peptide has the following sequence:
CSNLSTCVLGKLSQELHKLQTYPRTNTGSGTP-NH$_2$ [SEQ. ID. NO. 18] wherein the cysteine residues at positions 1 and 7 are linked by a disulfide linkage.

36. A hybrid peptide according to claim 32 or claim 33 wherein said CCK agonist peptide has the following sequence:
DY(OSO$_3$H)MGWMDF-NH$_2$ [SEQ. ID. NO. 19].

37. A hybrid peptide according to claim 32 or claim 33 wherein said CCK agonist peptide has the following sequence:
DYMGWMDF-NH$_2$ [SEQ. ID. NO. 20].

38. A hybrid peptide according to claim 32 or claim 33 wherein said CCK agonist peptide has the following sequence:
MGWMDF-NH$_2$ [SEQ. ID. NO. 21].

39. A hybrid peptide according to claim 32 or claim 33 wherein said CCK agonist peptide has the following sequence:
GWMDF-NH$_2$ [SEQ. ID. NO. 22].

40. A hybrid peptide according to claim 32 or claim 33 wherein said CCK agonist peptide has the following sequence:
WMDF-NH$_2$ [SEQ. ID. NO. 23].

41. A hybrid peptide according to claim 32 or claim 33 wherein said CCK agonist peptide has the following sequence:
KDY(OSO$_3$H)MGWMDF-NH$_2$ [SEQ. ID. NO. 24].

42. A hybrid peptide according to claim 32 or claim 33 wherein said CCK agonist peptide has the following sequence:
KDYMGWMDF-NH$_2$ [SEQ. ID. NO. 25].

43. A hybrid peptide according to claim 32 or claim 33 wherein said CCK agonist peptide has the following sequence:
KMGWMDF-NH$_2$ [SEQ. ID. NO. 26].

44. A hybrid peptide according to claim 32 or claim 33 wherein said CCK agonist peptide has the following sequence:
KGWMDF-NH$_2$ [SEQ. ID. NO. 27].

45. A hybrid peptide according to claim 32 or claim 33 wherein said CCK agonist peptide has the following sequence:
KWMDF-NH$_2$ [SEQ. ID. NO. 28].

46. A hybrid peptide composition comprising an amylin agonist peptide and a CCK agonist peptide covalently linked by the following structure:

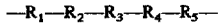

wherein said amylin agonist peptide and said CCK agonist peptide are linked via the $NH_2$ of the N-terminus or side chain $NH_2$ (provided that a side chain containing $NH_2$ is present in such peptide) of either peptide to $R_1$, and via a side chain carboxylic acid of either peptide (provided that a side chain containing an carboxylic acid group is present in such peptide) to $R_5$; and (a) $R_1$ is $CONH(CH_2)N$, $COO(CH_2)n$, or $CO(CH_2)n$, where n=1–6;
(b) $R_2$ is $COONH(CH_2)_n$ (where n=1–6), $COO(CH_2)_n$ (where n=1–6), $CO(CH_2)_n$ (where n=1–6), $OCO(CH_2)_n$ (where n=1–6), $NHCO(CH_2)_n$ (where n=1–6), $OCOC_6H_4$ (ortho, meta or para linked), $COOC_6H_4$ (ortho, meta or para linked), $COOC_6H_4O$ (ortho, meta or para substituted), $NHCOC_6H_4$ (ortho, meta or para linked), $NHCOC_6H_4O$ (ortho, meta or para substituted), $CONHC_6H_4NH$ (ortho, meta or para substituted), O—X (where X is any amino acid linked via its carboxyl group, and NH—X (where X is any amino acid liked via its carboxyl group);
(c) $R_3$ is $CH_2$, $CF_2$, CO, CS or CNH;
(d) $R_4$ is O or NH; and
(e) $R_5$ is $(CH_2)_n NH$ or $(CH_2)_n O$, where n=1–6.

47. A hybrid peptide composition comprising an amylin agonist peptide and a CCK agonist peptide covalently linked by the following structure:

wherein said amylin agonist peptide and said CCK agonist peptide are linked via the $NH_2$ of the N-terminus or side chain $NH_2$ (provided that a side chain containing $NH_2$ is present in such peptide) of either peptide to $R_1$, and via a side chain carboxylic acid of either peptide (provided that a side chain containing an carboxylic acid group is present in such peptide) to $R_2$; and (a) $R_1$ is $CONH(CH_2)_n$, $COO(CH_2)N$, or $CO(CH_2)N$; and
(b) $R_2$ is $(CH_2)_n NH$ or $(CH_2)_n O$, where n=1–6.

48. A hybrid peptide according to claim 46 or claim 47 wherein said amylin agonist peptide has the following sequence:
KCNTATCATQRLANFLVHSSNNFGPILPPTNVGSNT-Y-NH$_2$ [SEQ. ID. NO. 29] and wherein the cysteine residues at positions 2 and 7 are linked by a disulfide linkage.

49. A hybrid peptide according to claim 46 or claim 47 wherein said amylin agonist peptide has the following sequence:
KCNTATCATQKLANFLVHSSNNFGPILPPTNVGSNT-Y-NH2 [SEQ. ID. NO. 30] and wherein the cysteine residues at positions 2 and 7 are linked by a disulfide linkage.

50. A hybrid peptide according to claim 46 or claim 47 wherein said amylin agonist peptide has the following sequence:

CSNLSTCVLGKLSQELHKLQTYPRTNTGSGTP-NH$_2$ [SEQ. ID. NO. 31] wherein the cysteine residues at positions 1 and 7 are linked by a disulfide linkage.

51. A hybrid peptide according to claim 46 or claim 47 wherein said CCK agonist peptide has the following sequence:

DY(OSO$_3$H)MGWMDF-NH$_2$ [SEQ. ID. NO. 32].

52. A hybrid peptide according to claim 46 or claim 47 wherein said CCK agonist peptide has the following sequence:

DYMGWMDF-NH$_2$ [SEQ. ID. NO. 33].

53. A hybrid peptide according to claim 46 or claim 47 wherein said CCK agonist peptide has the following sequence:

MGWMDF-NH$_2$ [SEQ. ID. NO. 34].

54. A hybrid peptide according to claim 46 or claim 47 wherein said CCK agonist peptide has the following sequence:

GWMDF-NH$_2$ [SEQ. ID. NO. 35].

55. A hybrid peptide according to claim 46 or claim 47 wherein said CCK agonist peptide has the following sequence:

WMDF-NH$_2$ [SEQ. ID. NO. 36].

56. A hybrid peptide according to claim 46 or claim 47 wherein said CCK agonist peptide has the following sequence:

KDY(OSO$_3$H)MGWMDF-NH$_2$ [SEQ. ID. NO. 37].

57. A hybrid peptide according to claim 46 or claim 47 wherein said CCK agonist peptide has the following sequence:

KDYMGWMDF-NH$_2$ [SEQ. ID. NO. 38].

58. A hybrid peptide according to claim 46 or claim 47 wherein said CCK agonist peptide has the following sequence:

KMGWMDF-NH$_2$ [SEQ. ID. NO. 39].

59. A hybrid peptide according to claim 46 or claim 47 wherein said CCK agonist peptide has the following sequence:

KGWMDF-NH$_2$ [SEQ. ID. NO. 40].

60. A hybrid peptide according to claim 46 or claim 47 wherein said CCK agonist peptide has the following sequence:

KWMDF-NH$_2$ [SEQ. ID. NO. 41].

61. A hybrid peptide composition comprising an amylin agonist peptide and a CCK agonist peptide covalently linked by the following structure:

$$-R_1-R_2-R_3-R_4-R_5-$$

wherein said amylin agonist peptide and said CCK agonist peptide are linked via side chain carboxylic acid groups of both peptides (provided that a side chain containing an carboxylic acid group is present in such peptides); and (a) $R_1$ is NH(CH$_2$)$_n$ or O(CH$_2$)$_n$, where n=1–6;

(b) $R_2$ is OCO(CH$_2$)$_n$ (where n=1–6), NHCO(CH$_2$)$_n$ (where n=1–6), OCOC$_6$H$_4$ (ortho, meta or para linked), COOC$_6$H$_4$ (ortho, meta or para linked), COOC$_6$H$_4$O (ortho, meta or para substituted), NHCOC$_6$H$_4$ (ortho, meta or para linked), CONHC$_6$H$_4$ (ortho, meta or para substituted), CONHC$_6$H$_4$O (ortho, meta or para substituted), CONHC$_6$H$_4$NH (ortho, meta or para substituted), O—X (where X is any amino acid linked via its carboxyl group, and NH—X (where X is any amino acid liked via its carboxyl group);

(c) $R_3$ is CH$_2$, CF$_2$, CO, CS or CNH;

(d) $R_4$ is O or NH; and (e) $R_5$ is (CH$_2$)$_n$NHCO or (CH$_2$)$_n$O, where n=1–6.

62. A hybrid peptide composition comprising an amylin agonist peptide and a CCK agonist peptide covalently linked by the following structure:

$$-R_1-R_2-$$

wherein said amylin agonist peptide and said CCK agonist peptide are linked via side chain carboxylic acid groups of both peptides (provided that a side chain containing an carboxylic acid group is present in such peptides); and (a) $R_1$ is NH(CH$_2$)$_n$ or O(CH$_2$)$_n$; and (b) $R_2$ is (CH$_2$)$_n$NH or (CH$_2$)$_n$O, where n=1–6.

63. A hybrid peptide according to claim 61 or claim 62 wherein said amylin agonist peptide has the following sequence:

KCNTATCATQRLANELVHSSNNFGPILPPTNVGSNT-Y-NH$_2$ [SEQ. ID. NO. 42] and wherein the cysteine residues at positions 2 and 7 are linked by a disulfide linkage.

64. A hybrid peptide according to claim 61 or claim 62 wherein said amylin agonist peptide has the following sequence:

CSNLSTCVLGKLSQELHKLQTYPRTNTGSGTP-NH$_2$ [SEQ. ID. NO. 43] wherein the cysteine residues at positions 1 and 7 are linked by a disulfide linkage.

65. A hybrid peptide according to claim 61 or claim 62 wherein said CCK agonist peptide has the following sequence:

DY(OSO$_3$H)MGWMDF-NH$_2$ [SEQ. ID. NO. 44].

66. A hybrid peptide according to claim 61 or claim 62 wherein said CCK agonist peptide has the following sequence:

DYMGWMDF-NH$_2$ [SEQ. ID. NO. 45].

67. A hybrid peptide according to claim 61 or claim 62 wherein said CCK agonist peptide has the following sequence:

MGWMDF-NH$_2$ [SEQ. ID. NO. 46].

68. A hybrid peptide according to claim 61 or claim 62 wherein said CCK agonist peptide has the following sequence:

GWMDF-NH$_2$ [SEQ. ID. NO. 47].

69. A hybrid peptide according to claim 61 or claim 62 wherein said CCK agonist peptide has the following sequence:

WMDF-NH$_2$ [SEQ. ID. NO. 48].

70. A hybrid peptide according to any of claims 17, 32, 33, 46, 47, 61 or 62 wherein at least one hetero atom along the backbone of the linker is oxygen.

71. A hybrid peptide according to any of claims 17, 32, 33, 46, 47, 61 or 62 wherein all of the hetero atoms along the backbone of the linker are nitrogen.

72. A hybrid peptide composition comprising a molecule of the following structure:

$$R_1-C-R_2-C-R_3-R_4-R_5$$

wherein:

(a) $R_1$ is either a free N-terminus or an N-terminus amidated with acetamide, proionamide, butyramide, isobutyramide, or isocaproramide; or a lysine (L) amidated with acetamide, proionamide, butyramide, isobutyramide, or isocaproramide;

(b) $R_2$ is an amino acid sequence selected from NTAT [SEQ. ID. NO. 49], GTAT [SEQ. ID. NO. 50], NTVT [SEQ. ID. NO. 51], NMAT [SEQ. ID. NO. 52], SNLST [SEQ. ID. NO. 53], ASLST [SEQ. ID. NO. 54] AND GNLST [SEQ. ID. NO. 55];

(c) $R_3$ is an amino acid sequence selected from ATQRLANFLVH [SEQ. ID. NO. 56] and VLGKLSQELHK [SEQ. ID. NO. 57];

(d) $R_4$ is an amino acid sequence selected from SSNNFGPILPP [SEQ. ID. NO. 58] and LQTYPR [SEQ. ID. NO. 59]; and (e) $R_5$ is an amino acid sequence selected from DYMGWMDF-NH$_2$ [SEQ. ID. NO. 60], TNTGWMDF-NH$_2$ [SEQ. ID. NO. 61], TNVGWMDF-NH$_2$ [SEQ. ID. NO. 62], TNTGWLDF-NH$_2$ [SEQ. ID. NO. 63], TNVGWLDF-NH$_2$ [SEQ. ID. NO. 64], TNTGSNDF-NH$_2$ [SEQ. ID. NO. 65], TNVGSNDF-NH$_2$ [SEQ. ID. NO. 66], TNTGSNDY-NH$_2$ [SEQ. ID. NO. 67] and TNVGSNDY-NH$_2$ [SEQ. ID. NO. 68].

73. A composition comprising the following amino acid sequence:
KCNTATCATQRLANFLVHSSNNFGPILPPDYMGWMDF-NH$_2$ [SEQ. ID. NO. 69].

74. A composition comprising the following amino acid sequence:
CSNLSTCVLGKLSQELHKLQTYPRDYMGWMDF-NH$_2$ [SEQ. ID. NO. 70].

75. A composition comprising the following amino acid sequence:
KCNTATCATQRLANFLVHSSNNFGPILPPTNTGWM-DF-NH$_2$ [SEQ. ID. NO. 71].

76. A composition comprising the following amino acid sequence:
CSNLSTCVLGKLSQELHKLQTYPRTNTGWMDF-NH$_2$ [SEQ. ID. NO. 72].

77. A composition comprising the following amino acid sequence:
KCNTATCATQRLANFLVHSSNNFGPILPPTNTGWL-DF-NH$_2$ [SEQ. ID. NO. 73].

78. A composition comprising the following amino acid sequence:
CSNLSTCVLGKLSQELHKLQTYPRTNTGWLDF-NH$_2$ [SEQ. ID. NO. 74].

79. A composition comprising the following amino acid sequence:
KCNTATCATQRLANFLVHSSNNFGPILPPTNVGSN-DF-NH$_2$ [SEQ. ID. NO. 75].

80. A composition comprising the following amino acid sequence:
CSNLSTCVLGKLSQELHKLQTYPRTNVGSNDF-NH$_2$ [SEQ. ID. NO. 76].

81. A composition comprising the following amino acid sequence:
KCNTATCATQRLANFLVHSSNNFGPILPPTNVGSN-DY-NH$_2$ [SEQ. ID. NO. 77].

82. A composition comprising the following amino acid sequence:
CSNLSTCVLGKLSQELHKLQTYPRTNVGSNDY-NH$_2$ [SEQ. ID. NO. 78].

83. A method for suppressing food intake in a mammal comprising administering to said mammal a therapeutically effective amount of a composition of any of claims 1–6, 17, 18, 32, 33, 46, 47, 61, 63 or 72.

84. A method for control of appetite in a mammal comprising administering to said mammal a therapeutically effective amount of a composition of any of claims 1–6, 17, 18, 32, 33, 46, 47, 61, 63 or 72.

85. A method for control of body weight in a mammal comprising administering to said mammal a therapeutically effective amount of a composition of any of claims 1–6, 17, 18, 32, 33, 46, 47, 61, 63 or 72.

* * * * *